(12) United States Patent
Takoh

(10) Patent No.: US 9,340,829 B2
(45) Date of Patent: May 17, 2016

(54) METHOD OF DETECTING TARGET MATERIAL, SENSOR CHIP, AND DETECTING DEVICE

(75) Inventor: Kimiyasu Takoh, Tokyo (JP)

(73) Assignee: NEC Corporation, Tokyo (JP)

( * ) Notice: Subject to any disclaimer, the term of this patent is extended or adjusted under 35 U.S.C. 154(b) by 21 days.

(21) Appl. No.: 14/234,844

(22) PCT Filed: May 30, 2012

(86) PCT No.: PCT/JP2012/003538
§ 371 (c)(1),
(2), (4) Date: Jan. 24, 2014

(87) PCT Pub. No.: WO2013/014843
PCT Pub. Date: Jan. 31, 2013

(65) Prior Publication Data
US 2015/0050645 A1 Feb. 19, 2015

(30) Foreign Application Priority Data

Jul. 25, 2011 (JP) .................................. 2011-162023
Mar. 2, 2012 (JP) .................................. 2012-046589

(51) Int. Cl.
*C12Q 1/68* (2006.01)
*G01N 33/542* (2006.01)
(Continued)

(52) U.S. Cl.
CPC .............. *C12Q 1/6825* (2013.01); *B82Y 15/00* (2013.01); *C12Q 1/6823* (2013.01); *G01N 33/542* (2013.01); *G01N 33/588* (2013.01)

(58) Field of Classification Search
CPC ........... C12Q 1/6823; C12Q 2525/131; C12Q 2525/205; C12Q 2565/525; C12Q 1/6825
See application file for complete search history.

(56) References Cited

U.S. PATENT DOCUMENTS

2005/0176049 A1 8/2005 Watanabe
2008/0287666 A1 11/2008 Watanabe
2010/0204461 A1 8/2010 Beadling

FOREIGN PATENT DOCUMENTS

EP 1568997 A2 8/2005
EP 1992705 A1 11/2008
(Continued)

OTHER PUBLICATIONS

Baker, B. et al., "An Electronic, Aptamer-Based Small-Molecule Sensor for the Rapid, Label-Free Detection of Cocain in Adulterated Samples and Biological Fluids", American Chemical Society, vol. 128, 2006, pp. 3138-3139.

(Continued)

*Primary Examiner* — Teresa E Strzelecka
(74) *Attorney, Agent, or Firm* — Wilmer Cutler Pickering Hale and Dorr LLP

(57) ABSTRACT

A method of detecting a target material (3) includes: a step of preparing a complex (11), the complex including an aptamer (1) to which a target material (3) in a specimen specifically binds, a first nucleic acid fragment (2) that has a base sequence complementary to the aptamer (1), and a fixing member (4) to which a part of the aptamer (1) and a part of the first nucleic acid fragment (2) are fixed, in which the aptamer (1) has a double strand-forming site (5) capable of forming a double strand with the first nucleic acid fragment (2); a step of separating the first nucleic acid fragment (2) from the double strand-forming site (5) of the aptamer (1) by binding the target material (3) to the aptamer (1); and a step of detecting the cleavage of the double strand.

8 Claims, 20 Drawing Sheets

(a)

(b)

(c)

(d)

(51) Int. Cl.
*G01N 33/58* (2006.01)
*B82Y 15/00* (2011.01)
*C07H 21/02* (2006.01)

(56) References Cited

FOREIGN PATENT DOCUMENTS

| JP | 2003-508729 | A | 3/2003 |
|---|---|---|---|
| JP | 2005-257667 | A | 9/2005 |
| JP | 2008-278837 | A | 11/2008 |
| JP | 4576945 | B2 | 11/2010 |
| WO | WO-2008/048310 | A2 | 4/2008 |

OTHER PUBLICATIONS

International Search Report corresponding to International Application No. PCT/JP2012/003538, Aug. 24, 2012, 2 pages.
Kim, N., et al., "Reversible Tuning of SERS Hot Spots with Aptamers", Adv. Matter. Aug. 2011, vol. 23, pp. 4152-4156.
Li, J., et al., "Aptamer-quantum Dots Conjugates-based Ultrasensitive Competitive Electrochemial Cytosensor for the Detection of Tumor Cell", Talanta, Jul. 21, 2011, vol. 85, pp. 2113-2120.
Li, X., et al., "Multianalyte Electrochemical Biosensor Based on Aptamer- and Nanparticle-Integrated Bio-Barcode Amplification", Chem. Asian Journal, 2010, vol. 5, pp. 294-300.
Liu, J., et al., "Smart Nanomaterials Responsive to Multiple Chemical Stimuli with Controllable Cooperativity", Adv. Mater., 2006, vol. 18, pp. 1667-1671.
Liu, Z., et al., "Highly Sensitive, Reusable Electrochemical Aptasensor for Adenosine" Electrochimica Acta, 2009, vol. 54, pp. 6207-6211.
Markham, N., et al., "DINAMelt Web Server for Nucleic Acid Melting Prediction", Nucleic Acids Research, 2005, vol. 33, pp. 577-581.
Xiao, Y., et al., "A Reagentless Signal-On Architecture for Electronic, Aptamer-Based Sensors via Target-Induced Strand Displacement", J. American Chemical Society, 2005, vol. 127, pp. 17990-17991.
Xiao, Y., et al., "Label-Free Electronic Detection of Thrombin in Blood Serum by Using an Aptamer-Based Sensor", Angew. Chem. Int. Ed., 2005, vol. 44, pp. 5456-5459.
Xu, H., et al., "Aptamer-Functionalized Gold Nanparticles as Probes in a Dry-Reagent Strip Biosensor for Protein Analysis", Analytical Chemistry, vol. 81, 2009, pp. 669-675.

FIG. 1
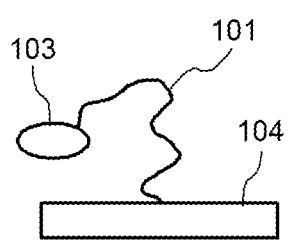
(a)
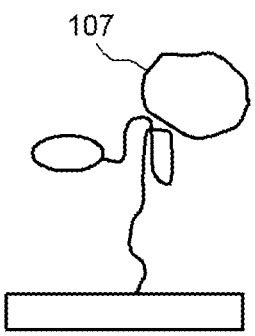
(b)
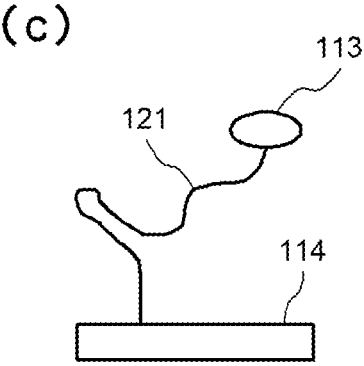
(c)
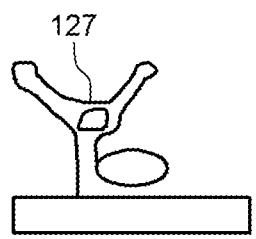
(d)

FIG. 2
(a)
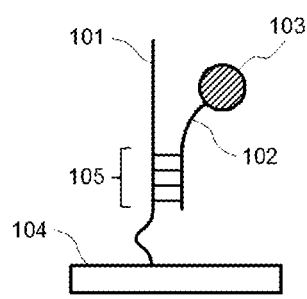
(b)
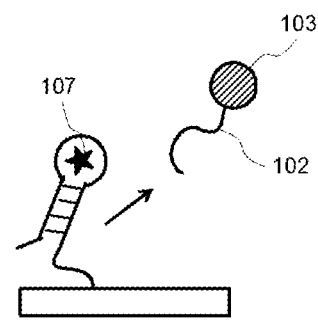

FIG. 3
(a) 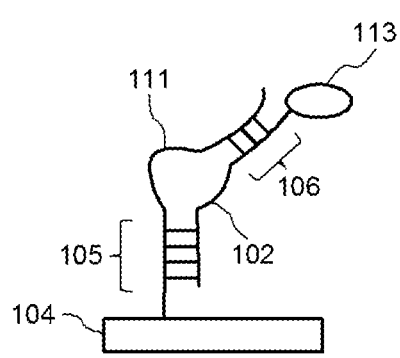
(b) 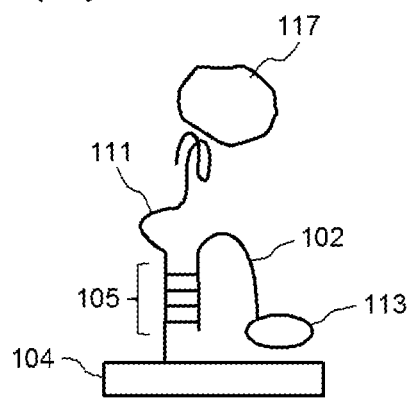

FIG. 9
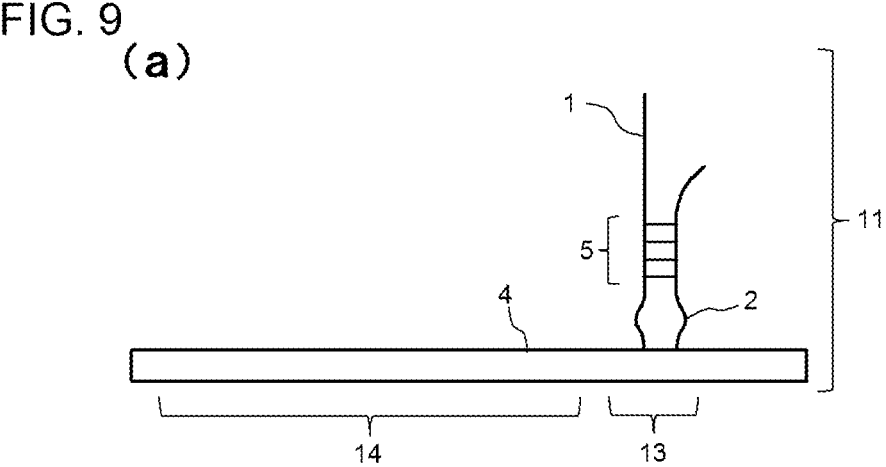
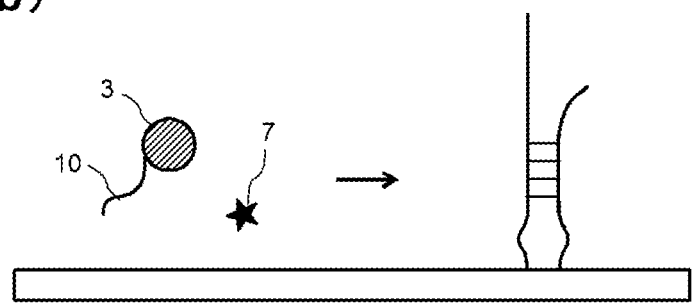
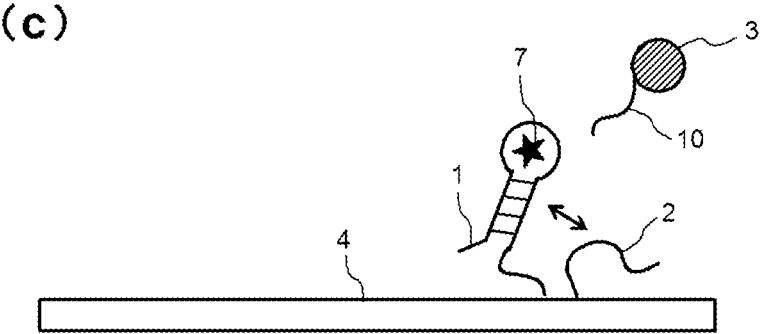
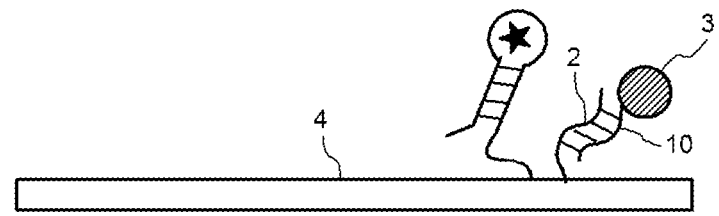

FIG. 11
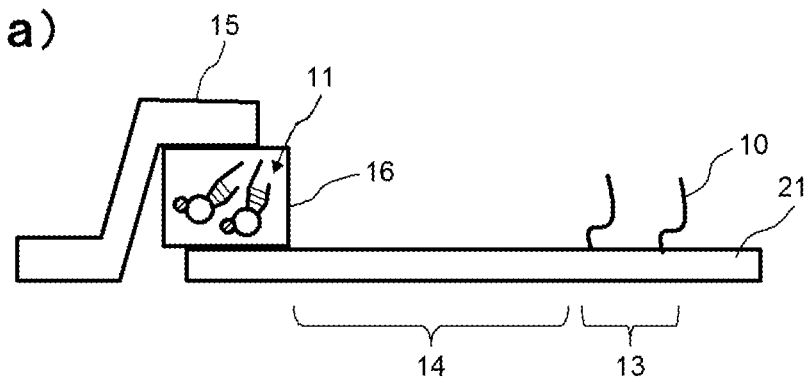
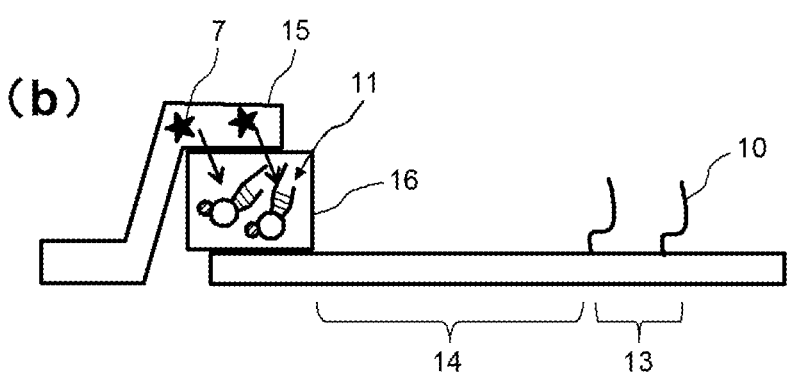
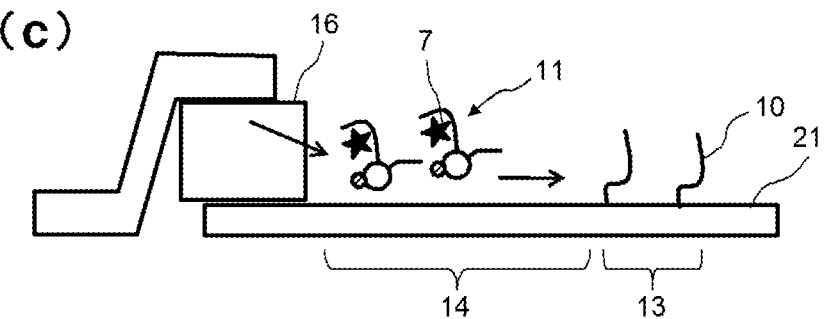
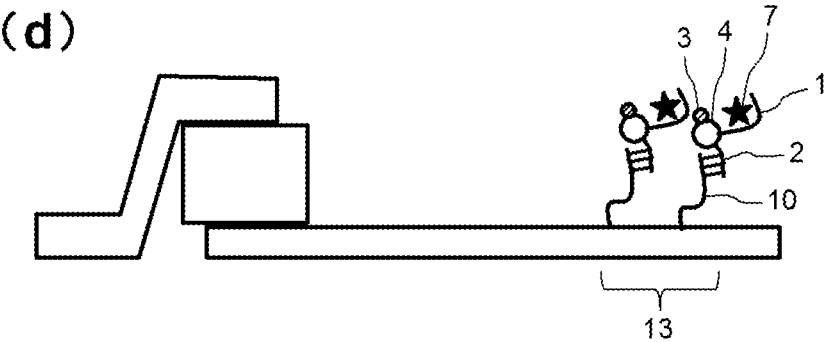

FIG. 15

| | | |
|---|---|---|
| SEQUENCE 1 | 5' | ACCTGGGGGAGTATTGCGGAGGAAGGT  3' |
| SEQUENCE 2 | 5' | HS-CACTGACCTGGGGGAGTATTGCGGAGGAAGGT  3' |
| SEQUENCE 3 | 3' | HS-TCTCTTGGACCC - [MB] 5' |
| SEQUENCE 4 | 5' | CCCAGGTTCTCTTTTTTTTTACCTGGGGGAGTATTGCGGAGGAAGGT  3' |
| SEQUENCE 5 | 3' | GGGTCCAAGAGA 5' |
| SEQUENCE 6 | 5' | CCCAGGTTCTCTTTTTTTTT  3' |
| SEQUENCE 7 | 3' | HS-TCTCTTGGACCCCC - [MB] 5' |
| SEQUENCE 8 | 3' | HS-TCTCTTGGAC - [MB] 5' |
| SEQUENCE 9 | 5' | HS-TTCACTGACCTGGGGGAGTATTGCGGAGGAAGGT  3' |
| SEQUENCE 10 | 5' | HS-CTGACCTGGGGGAGTATTGCGGAGGAAGGT  3' |
| SEQUENCE 11 | 5' | HS-GACCTGGGGGAGTATTGCGGAGGAAGGT  3' |
| SEQUENCE 12 | 3' | HS-TTTCTCTTGGACCC-[MB] 5' |
| SEQUENCE 13 | 3' | HS-TCTTGGACCC-[MB] 5' |
| SEQUENCE 14 | 3' | HS-TTGGACCC-[MB] 5' |
| SEQUENCE 15 | 5' | HS-AGAGAACCTGGGGGAGTATTGCGGAGGAAGGT  3' |

FIG. 16

|  | DOUBLE-STRANDED NUCLEIC ACID FORMING RATIO (%) |
|---|---|
| SEQUENCE 4 AND SEQUENCE 5 | 2 |
| SEQUENCE 5 AND SEQUENCE 6 | 8 5 | ns
METHOD OF DETECTING TARGET MATERIAL, SENSOR CHIP, AND DETECTING DEVICE

CROSS-REFERENCE TO RELATED APPLICATIONS

This application is a national stage application of International Application No. PCT/JP2012/003538 entitled "Method of Detecting Target Material, Sensor Chip, and Detecting Device," filed on May 30, 2012, which claims the benefit of the priority of Japanese patent application 2011-162023, filed on Jul. 25, 2011, and Japanese patent application 2012-046589, filed on Mar. 2, 2012, the disclosures of each of which are hereby incorporated by reference in their entirety.

SEQUENCE LISTING

The instant application contains a Sequence Listing which has been submitted electronically in ASCII format and is hereby incorporated by reference in its entirety. The ASCII copy is named 2209611.130US1_SL.txt, and is 4,266 bytes in size. This ASCII copy contains the same Sequence Listing submitted when the instant application was originally filed and is being submitted in a different format.

TECHNICAL FIELD

The present invention relates to a method of detecting a target material, a sensor chip, and a detecting device.

BACKGROUND ART

Aptamers refer to nucleic acids (DNA, RNA, and PNA) having an ability to bind to a specific material. Binding target materials (hereinafter, also referred to as "target material) of the aptamers include a wide variety of materials, for example, biomolecules such as proteins, hormones, and peptides; artificial molecules such as agricultural chemicals; and small molecules such as potassium ions. Therefore, a target material contained in a specimen can be quantitatively measured by detecting a bond between an aptamer and the target material. In addition, a sensor which specifically responds to a target material can be constructed by extracting a bond between an aptamer and the target material as an electric signal.

When a target material is detected using an aptamer, there are advantageous effects in that, for example, an aptamer is easily handled during solution exchange or the like, and a large number of aptamers are easily handled at the same time. Therefore, there are cases where an aptamer may be used while being held on a solid body (for example, Patent Documents 1 and 2 and Non-Patent Documents 1 to 4).

For example, Non-Patent Documents 1 and 2 disclose sensors in which aptamers 101 and 121 labeled with methylene blues, which are electrode reactants 103 and 113, are fixed on electrodes 104 and 114 (FIGS. 1(*a*) to 1(*d*)). Using a bond with a target material (a target material 107 such as thrombin or a cocaine 127), these sensors detect conformational changes occurring in the aptamers 101 and 121 as changes in distance between the electrodes 104 and 114 and the electrode reactants 103 and 113, that is, as changes in the reaction currents of the electrode reactants 103 and 113. However, as clearly seen from a schematic diagram of FIG. 1, the pattern and amount of a conformational change of an aptamer caused by a bond with a target material vary depending on aptamers. That is, as illustrated in FIG. 1(*c*), after a conformational change of the aptamer 121, the electrode reactant 113 may be separated from the electrode 114. On the other hand, as illustrated in FIG. 1(*d*), after a conformational change of the aptamer 121, the electrode reactant 113 may approach the electrode 114. Therefore, when a distance between a labeling material and an electrode is greatly changed by chance and is used in a sensor with a method disclosed in Non-Patent Documents 1 and 2, an aptamer capable of obtaining a sufficient signal change becomes limited. That is, the techniques of Non-Patent Documents 1 and 2 have a room for improvement in terms of detection accuracy.

Patent Document 1 discloses a technique in which a mechanism for detecting the existence of a target material is improved. That is, Patent Document 1 discloses an aptamer sensor using the aptamer 101 and a complementary strand 102 thereof as illustrated in FIG. 2. According to Patent Document 1, the existence of a target material can be detected according to the following mechanism. That is, in the aptamer sensor, the aptamer 101 and the complementary strand 102 form complementary base pairs to form a double-stranded nucleic acid region (double strand-forming site 105) (FIG. 2(*a*)) in the absence of the target material. In this double-stranded nucleic acid region, when the target material 107 exists, the formation of the complementary base pairs is dissociated and eliminated (FIG. 2(*b*)) by the aptamer 101 and the target material 107 binding to each other. By detecting changes in physical and chemical properties caused by the dissociation, the target material is detected. For example, Patent Document 1 discloses that the existence of a target material can be detected by detecting the separation of the complementary strand 102 having the electrode reactant 103 from the electrode 104 (surface plasmon resonance sensor substrate).

RELATED DOCUMENT

Patent Document

[Patent Document 1] Japanese Unexamined patent publication No. 2008-278837
[Patent Document 2] PCT Japanese Translation Patent Publication No. 2003-508729

Non-Patent Document

[Non-Patent Document 1] Yi Xiao, et al., Angew. Chem. Int. Ed., 2005, No. 44, pp. 5456 to 5459
[Non-Patent Document 2] Brian R Baker, et al., Journal of American chemical society, 2006, No. 128, pp. 3138 to 3139
[Non-Patent Document 3] Yi Xiao, et al., Journal of American chemical society, 2005, No. 127, pp. 17990 to 17991
[Non-Patent Document 4] Juewen Liu, et al., Advanced materials, 2006, No. 18, pp. 1667 to 1671
[Non-Patent Document 5] Markham, N. R. et al., Nucleic Acids Research, 2005, No. 33, pp. 577 to 581
[Non-Patent Document 6] Hui Xu, et al., Analytical chemistry, 2009, No. 81, pp. 669 to 675

SUMMARY OF THE INVENTION

Problems to be Solved by the Invention

As a result of study, the present inventors found that the above-described technique disclosed in Patent Document 1 has a room for improvement in achieving both contradictory properties: a double-strand holding ability during the non-binding of a target material; and a double-strand cleaving ability during the binding of a target material.

That is, in order to efficiently detect a target material in a specimen, it is necessary that a double strand between an aptamer and a complementary strand be held before the target material binds to the aptamer. However, when a binding strength between the aptamer and the complementary strand is insufficient, the double strand is dissociated according to a dissociation equilibrium reaction. As a result, the complementary strand is separated from the aptamer and diffused in a solution of the specimen. In addition, there is a low possibility that the complementary strand diffused in the solution binds to the aptamer again. Therefore, the number of double strands between the aptamer and the complementary strand is gradually decreased, which may inhibit the detection of a target material.

Meanwhile, in order to compensate for the insufficiency of the binding strength between the aptamer and the complementary strand, a configuration of increasing the number of bases where the aptamer and the complementary strand are hybridized can be considered. However, when the number of bases is excessively increased in a double strand-forming region, a double strand is difficult to cleave. Therefore, the detection of a target material may be inhibited.

Accordingly, the design of a double strand-forming site of an aptamer of the related art is extremely difficult to make due to such contradictory properties as a double strand holding ability and a double strand cleaving ability.

The present invention has been made in consideration of the above-described circumstances, and an object thereof is to provide a method of detecting a target material with high reliability by using an aptamer in which the two mutually contradictory properties are improved and a nucleic acid fragment.

BRIEF SUMMARY OF THE INVENTION

According to the present invention, there is a method of detecting a target material, the method including:
a step of preparing a complex, the complex including
an aptamer to which a target material in a specimen specifically binds,
a first nucleic acid fragment that has a base sequence complementary to the aptamer, and
a fixing member to which a part of the aptamer and a part of the first nucleic acid fragment are fixed,
in which the aptamer includes a double strand-forming site capable of forming a double strand with the first nucleic acid fragment;
a step of separating the first nucleic acid fragment from the double strand-forming site of the aptamer by binding the target material to the aptamer; and
a step of detecting the cleavage of the double strand where the first nucleic acid fragment is separated from the aptamer.

Further, according to the present invention, there is provided a sensor chip which is used for detecting a target material, comprising a complex,
wherein the complex includes
an aptamer to which a target material in a specimen specifically binds,
a first nucleic acid fragment that has a base sequence complementary to the aptamer, and
a fixing member to which a part of the aptamer and a part of the first nucleic acid fragment are fixed, and
the aptamer has a double strand-forming site capable of forming a double strand with the first nucleic acid fragment.

According to the present invention, there is provided a device of detecting a target material including:
the above-described sensor chip;
a binding portion that binds the target material to the aptamer; and
a detecting portion that detects the cleavage of the double strand.

Advantageous Effects of the Invention

According to the present invention, a method of detecting a target material with high reliability is provided.

BRIEF DESCRIPTION OF THE DRAWINGS

The above-described objects and other objects, characteristics, and advantageous effects will be further clearly described based on the following preferred embodiments and accompanying drawings.

FIG. 1 is a diagram illustrating the procedure of a method of detecting a target material in the related art.

FIG. 2 is a diagram illustrating the procedure of a method of detecting a target material in the related art.

FIG. 3 is a diagram illustrating the procedure of a method of detecting a target material in the related art.

FIG. 9 is a diagram illustrating the procedure of a method of detecting a target material according to a fourth exemplary embodiment.

FIG. 11 is a diagram illustrating the procedure of a method of detecting a target material according to the fifth exemplary embodiment.

FIG. 15 is a table illustrating the DNA sequences of Examples 1 to 5.

FIG. 16 is a table illustrating the simulation results of Example 2.

DESCRIPTION OF EXEMPLARY EMBODIMENTS

Figure 4:
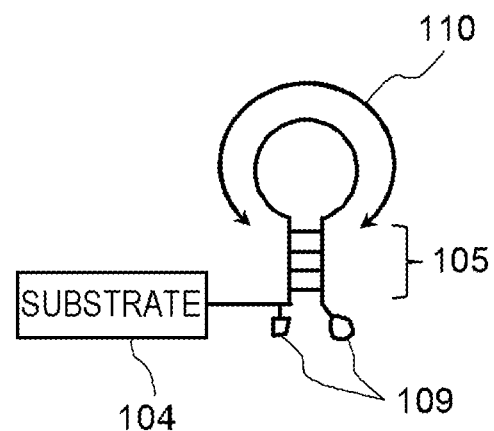
FIG. 4 is a diagram illustrating an aptamer beacon of a method of detecting a target material in the related art.

Hereinafter, embodiments of the present invention will be described using the drawings. In all the drawings, the same components are represented by the same reference numerals, and the description thereof will not be repeated.

First Exemplary Embodiment

Figure 6:
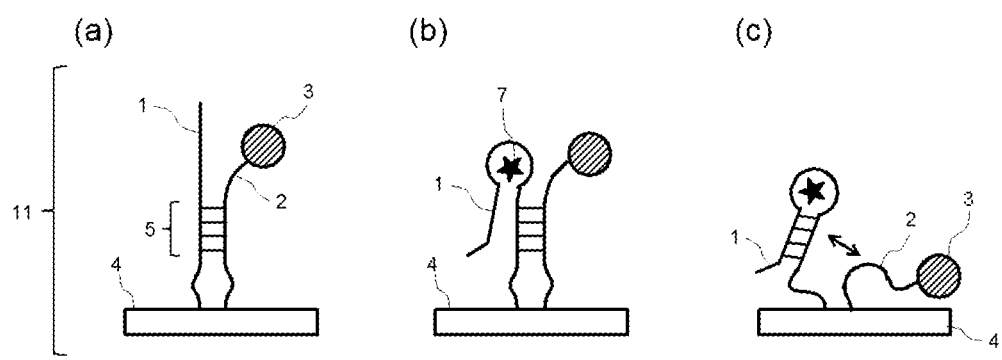
FIG. 6 is a diagram illustrating the procedure of a method of detecting a target material according to a first exemplary embodiment.

A first exemplary embodiment will be described using FIG. 6.

In this embodiment, examples of a method of detecting a target material according to the present invention and of a sensor for detecting a target material according to the present invention will be described.

A method of detecting a target material 7 according to the first exemplary embodiment includes the following steps. First, a complex 11 is prepared. The complex 11 includes an aptamer 1, a first nucleic acid fragment 2, and a fixing member 4. The target material 7 in a specimen (inspection target) specifically binds to the aptamer 1. In addition, the aptamer 1 has a double strand-forming site 5 capable of forming a double strand with the first nucleic acid fragment 2. The first nucleic acid fragment 2 has a base sequence complementary to the aptamer 1. A part of the aptamer 1 and a part of the first nucleic acid fragment 2 are fixed to the fixing member 4. Next, the target material 7 binds to the aptamer 1. Then, the first nucleic acid fragment 2 is separated from the aptamer 1 to detect the cleavage of a double strand. In this embodiment, the cleavage of a double strand refers to the first nucleic acid fragment 2 being separated from the double strand-forming site 5 of the aptamer 1, for example, in a state where the first nucleic acid fragment 2 is fixed to the fixing member 4.

In addition, being fixed to the fixing member 4 refers to binding by a chemical bond and/or a chemical adsorption other than a hydrogen bond forming a double strand. In addition, as a method of detecting the cleavage of a double strand, various well-known methods can be used, and the details thereof will be described below.

In this embodiment, the aptamer 1 has the double strand-forming site 5 capable of forming a double strand with the first nucleic acid fragment 2. Further, a part of the first nucleic acid fragment 2 is fixed to the fixing member 4 in the same manner as that of a part of the aptamer 1. Even if the first nucleic acid fragment 2 is separated from the aptamer 1 during the non-bonding of the target material 7, a part thereof is fixed to the fixing member 4. Therefore, it is difficult for the first nucleic acid fragment 2 to be diffused in a solution as in the related art. This first nucleic acid fragment 2 can form a double strand again with the aptamer 1. Therefore, unlike the related art, it is not necessary that the number of bases in the double strand-forming site 5 be increased to improve a double-strand holding ability. Accordingly, the double strand-forming site 5 of the aptamer 1 can be designed to be suited for a double-strand cleaving ability.

As described above, the double-strand holding ability is realized by fixing a part of the first nucleic acid fragment 2 to the fixing member 4, independently of the double strand-forming site 5 of the aptamer 1. That is, the double-strand holding ability and the double-strand cleaving ability are imparted to not only the double strand-forming site but also other portions. The double-strand holding ability can be imparted to a part of the fixed first nucleic acid fragment 2, and the double-strand cleaving ability can be imparted to the double strand-forming site 5. As a result, the two functions can be distributed to different portions. Therefore, according to the complex 11 of this embodiment, the double-strand holding ability and the double-strand cleaving ability which are mutually contradictory properties in the related art can be achieved at the same time. By using this complex 11, the target material can be detected with high reliability.

In addition, the method of detecting a target material according to this embodiment includes: a preparation step of preparing a complex in which the aptamer 1 to which a target material specifically binds and the nucleic acid fragment (first nucleic acid fragment 2) that has a base sequence complementary to the aptamer are fixed to the same member by a chemical bond and a chemical adsorption; a contact step of bringing the complex into contact with a specimen; a binding step of binding a target material in the specimen to the aptamer; a cleavage step of cleaving a double-stranded nucleic acid site formed by the aptamer and the nucleic acid fragment on the member; and a detection step of detecting the double-stranded nucleic acid site formed by the aptamer and the nucleic acid fragment.

Hereinafter, the step of detecting a target material according to this embodiment will be described in detail.

First, the complex 11 is prepared. This complex 11 includes the aptamer 1, the first nucleic acid fragment 2, and the fixing member 4. An end of the aptamer 1 and an end of the first nucleic acid fragment 2 are fixed to the fixing member 4 by a chemical bond and a chemical adsorption. In this embodiment, an end of the aptamer 1 and an end of the first nucleic acid fragment 2 are directly fixed to the fixing member 4. Further, at least a part in a base sequence of the aptamer 1 capable of forming a bond with the target material forms the double strand-forming site 5 with the first nucleic acid fragment 2 (FIG. 6(a)). In addition, a labeling material 3 binds to a tip of the first nucleic acid fragment 2. In the first exemplary embodiment, the double strand-forming site 5 (double-stranded nucleic acid site) refers to a site where an aptamer and a nucleic acid having a sequence complementary to the aptamer form a double strand of nucleic acid.

Next, for convenience of description, the step of preparing the complex 11 to the step of detecting the target material 7 are divided into the following first step and second step.

In the first step of the first exemplary embodiment, the target material 7 binds to the aptamer 1 (FIG. 6(b)). In the complex 11, a part in a base sequence of the aptamer 1 capable of forming a bond with the target material forms the double strand-forming site 5, but the other sites are in the single-stranded state. That is, a structure of the single-stranded sites of the aptamer 1 can be freely changed. In other words, the aptamer 1 includes the double strand-forming site 5 forming a double strand with the first nucleic acid fragment 2 and includes a binding site having a binding ability to the target material 7. Accordingly, the aptamer 1 can have a three-dimensional structure as an aptamer and can bind to the target material 7 in an inspection target.

Next, in the second step according to the first exemplary embodiment, a double strand in the double strand-forming site 5 which is formed between the aptamer 1 and the first nucleic acid fragment 2 is cleaved. That is, when the aptamer 1 and the target material 7 bind to each other in the first step, branch migration occurs, which eliminates the double strand-forming site 5. This branch migration occurs when a bond between the target material 7 and the aptamer 1 is stronger than a bond between nucleic acids which form the double-stranded nucleic acid site of the aptamer 1. When the double-stranded nucleic acid site of the aptamer 1 is eliminated in this way, the aptamer 1 is dissociated from the first nucleic acid fragment 2 (FIG. 6(*c*)). The first nucleic acid fragment 2 holds the state of being fixed to the fixing member 4 even after being separated from the aptamer 1. In this case, the base sequence of the aptamer 1 binding to the target material 7 is shared with a part or the entire portion of a base sequence of the double strand-forming site of the aptamer 1. Therefore, when the target material 7 binds to the aptamer 1, a structure of the double-stranded nucleic acid site of the aptamer 1 is changed, and the aptamer 1 and the first nucleic acid fragment 2 are cleaved.

Next, the cleavage of the double strand-forming site of the aptamer 1 is detected. In this case, the detection of the cleavage of the double strand-forming site of the aptamer 1 is not limited as long as physical and chemical changes caused by the cleavage of a double strand in the double-stranded nucleic acid site can be detected. For example, the detection refers to the detection of changes in signals such as optical signals, electrical signals, and color signals.

Here, the effects of the first exemplary embodiment will be described while being compared to the technique disclosed in Patent Document 1.

Patent Document 1 discloses that either an aptamer or a nucleic acid fragment is directly fixed to a member. That is, Patent Document 1 discloses that, when the aptamer is directly fixed to the member, the nucleic acid fragment forms a double strand with the aptamer to be fixed to the aptamer without being fixed to the member.

Here, a case where a binding strength between an aptamer and a nucleic acid fragment is insufficient will be described. In this case, even if the target material does not exist, a double-stranded nucleic acid site is eliminated in response to a dissociation equilibrium reaction of a double strand. After the elimination of the double-stranded nucleic acid site, a nucleic acid which is not fixed is immediately diffused in a solution and moves away from the surface of the member. Therefore, once the double-stranded nucleic acid site is eliminated, the possibility that the double-stranded nucleic acid site may be formed again is extremely low. Accordingly, even if the target material does not exist, the double-stranded nucleic acid site is decreased over time, which inhibits the detection of the target material.

Therefore, in order to form a stable double-stranded nucleic acid site, an excess number of bases are necessary. However, a binding strength between the excess number of bases inhibits conformational changes which cause the aptamer of the double-stranded nucleic acid site to have a double-helix structure and to bind to the target material. Therefore, when the double-stranded nucleic acid site is excessively long, there is a problem in that a binding strength of the aptamer to the target material deteriorates.

On the other hand, in the first exemplary embodiment, the aptamer 1 and the first nucleic acid fragment 2 are fixed to the same fixing member 4 by a chemical bond or a chemical adsorption, and thus nucleic acids thereof are locally concentrated on the surface of the member. As a result, the aptamer 1 and the first nucleic acid fragment 2 are more frequently brought into contact with each other, and an apparent binding constant is increased. Accordingly, in the aptamer 1 according to the first exemplary embodiment, the length of the double strand-forming site 5 required for stably forming the double-stranded nucleic acid state can be decreased, and thus an adverse effect of the double strand-forming site on the binding strength is decreased.

In addition, a technique in which only an aptamer is directly fixed to a member is disclosed in, for example, not only Patent Document 1 but also Non-Patent Document 3. In Non-Patent Document 3, a thrombin aptamer 111 is fixed to an electrode 104. A complementary strand 102 forms double strands with the thrombin aptamer 111 in two double strand-forming sites 105 and 106. This complementary strand 102 is labeled with methylene blue (electrode reactant 113) (FIG. 3(*a*)). Next, when a thrombin 117 is added, the double strand-forming site 106 is eliminated (FIG. 3(*b*)). The mobility of methylene blue is improved. The reaction current of methylene blue is improved, and thus the thrombin 117 is detected. However, in this method, even if thrombin is added, the double strand-forming site 105 is not completely eliminated. Therefore, the improvement in the mobility of methylene blue before and after the addition of thrombin is small, and the amount of a current change is also small (approximately 1% to 2% with respect to a base current).

On the other hand, in this embodiment, the double strand-forming site 5 is one. Therefore, after the double strand of the double strand-forming site 5 is cleaved, the first nucleic acid fragment 2 can freely move with respect to the aptamer 1. That is, the first nucleic acid fragment 2 does not form a double strand with the aptamer 1 after the target material 7 binds to the aptamer 1. On the other hand, in Non-Patent Document 3, the complementary strand 102 form a double strand with the thrombin aptamer 111 in the double strand-forming site 105 after the thrombin 117 binds to the thrombin aptamer 111. The first nucleic acid fragment 2 according to this embodiment does not include a portion which binds to a predetermined region of the double strand-forming site 5, and thus can freely move with respect to the aptamer 1 correspondingly. Therefore, the mobility of the labeling material 3 according to this embodiment is improved as compared to Non-Patent Document 3, and the amount of a current change of this embodiment is increased. Accordingly, according to this embodiment, a method of measuring a target material with high detection accuracy can be realized.

In the method of detecting a target material according to the first exemplary embodiment, the chemical bond and the chemical adsorption does not include a bond between nucleic acids by a hydrogen bond, for example, the formation of complementary base pairs. The reason is as follows. By nucleic acids being fixed to each other by a hydrogen bond, a three-dimensional structure between an aptamer and a nucleic acid fragment is changed. As a result, the double strand-forming site 5 cannot be sufficiently formed, or a bond between the aptamer 1 and the target material 7 may be inhibited. Therefore, the detection of the target material 7 is inhibited.

In addition, Patent Document 2 discloses an aptamer sensor array (FIG. 4) in which an end of an aptamer with a mechanism of a molecular beacon incorporated is fixed to a substrate (electrode 104). In addition, a modifier 109 binds to a terminal of the aptamer. The modifier 109 for causing the beacon to function may inhibit a bond with the aptamer due to steric hindrance and the like. In order to avoid such hindrance, a sequence near the center of the aptamer forms a double strand formation-prohibited site 110. The double strand formation-prohibited site 110 has a limitation in that it cannot be used as the double-stranded nucleic acid region for causing the beacon mechanism to operate.

Figure 5:
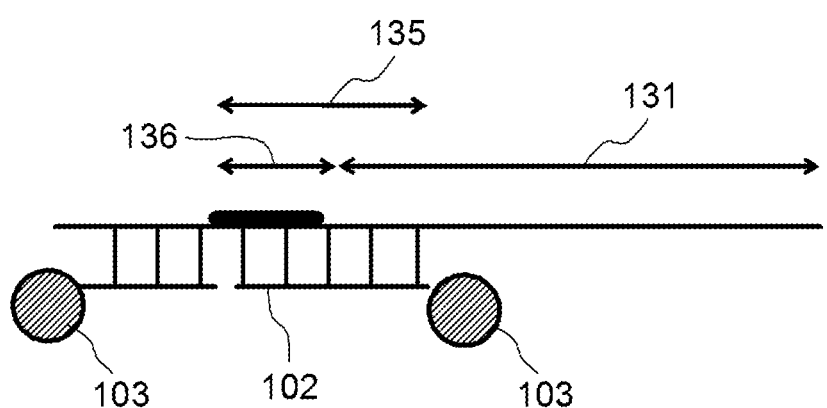
FIG. 5 is a diagram illustrating a probe design method of a method of detecting a target material in the related art.

Further, Non-Patent Document 4 discloses an aptamer in which a base sequence (margin sequence 136) having no relation with a binding strength of the aptamer is added to an extended area of an aptamer sequence 131 (FIG. 5). Non-Patent Document 4 discloses that, by using a part of a double strand-forming site 135 as the margin sequence 136, hybridizing and the binding strength of the aptamer are well-balanced. However, in this case, a site to which the margin sequence 136 can be added is limited to an end of the aptamer. Therefore, the margin sequence 136 has a limitation in that, for example, it cannot be applied to an aptamer having a larger conformational change at the center than that at an end.

In other words, when a margin sequence having no relation with a binding strength of an aptamer is added to an extended area of an aptamer sequence to be used as a part of a double-stranded nucleic acid site, the number of bases of the aptamer which are used for forming the double-stranded nucleic acid site is decreased. Therefore, an adverse effect of the double-stranded nucleic acid site on the binding strength can be decreased. On the other hand, when a margin sequence is added to the middle of an aptamer sequence, a binding strength of an aptamer deteriorates. Therefore, a forming position of a double-stranded nucleic acid site is limited to an end of an aptamer. Accordingly, for example, in an aptamer where a bond with the target material causes a large conformational change in a sequence at the center of the aptamer, a double-stranded nucleic acid site cannot be formed on the sequence at the center. Therefore, there is a limitation in that this conformational change cannot be efficiently used.

On the other hand, the base sequence of the double strand-forming site 5 of the aptamer 1 according to the embodiment can be made not to contain a margin sequence. In other words, the double strand-forming site 5 of the aptamer 1 has only a base sequence complementary to the base sequence of the first nucleic acid fragment 2. As a result, the double strand-forming site 5 can also be set in a portion other than an end of an aptamer. That is, the double strand-forming site 5 can be formed in portions where cleavage is likely to occur in the presence of the target material 7, for example, where a conformational change is large when the aptamer binds to the target material 7. Accordingly, a large signal change can be obtained.

As described above, in a method of the related art, there is a limitation for designing a sequence to cause an aptamer, which is held on a solid body, to effectively function. This limitation inhibits a wide variety of aptamers from being used for detecting a target material.

On the other hand, according to the first exemplary embodiment, as compared to the above-described Patent Documents, there is little limitation for designing a sequence when an aptamer is used as a sensor, and a wide variety of aptamers can be used for detecting a target material.

In addition, in the first exemplary embodiment, when an inspection target does not contain a material binding to the aptamer 1, the aptamer does not bind to a material in the inspection target, and a double strand 5 in the double strand-forming site is not eliminated. Accordingly, whether or not the inspection target contains the target material 7 can be detected by detecting the cleavage of the double-stranded nucleic acid site formed between the aptamer 1 and the first nucleic acid fragment 2.

In the method of detecting a target material according to the first exemplary embodiment, the aptamer 1 is a nucleic acid capable of specifically binding to the target material 7 and only needs to have a complementary base sequence capable of forming the double strand-forming site 5 with the first nucleic acid fragment 2. This aptamer 1 may be, for example, DNA or RNA, or an artificial nucleic acid such as PNA. The aptamer 1 is not particularly limited, but preferably has a structure of an aptamer that specifically binds to an epitope of the target material 7. In addition, the aptamer 1 may have a structure having a part that does not bind to the target material 7. The aptamer 1 can be obtained using a well-known aptamer screening method such as a SELEX method. In addition, optionally, an aptamer in which a desired base sequence is added to a nucleic acid sequence obtained by SELEX or the like may be synthesized. By adding the base sequence, a distance between an aptamer and a substrate can be increased to decrease steric hindrance, or the length of the double-strand nucleic acid site between the aptamer 1 and the complementary strand (the first nucleic acid fragment 2) can be adjusted to adjust the intensity of a binding strength between both. The double strand-forming site 5 between the aptamer 1 and the first nucleic acid fragment 2 may be posit6ioned at any portion of the aptamer 1, for example, at an end or the center of the aptamer. In addition, the entire sequence of a single-stranded nucleic acid of the aptamer 1 may form the double strand-forming site 5. However, when the target material 7 binds to the aptamer 1, branch migration is likely to occur in the double strand-forming site 5. Therefore, it is preferable that the double strand-forming site 5 has a part of a base sequence binding to the target material 7, and the length of the base sequence is preferably 2 bases to 20 bases, more preferably 4 bases to 15 bases, and still more preferably 6 bases to 12 bases. In addition, the aptamer 1 may be optionally modified with the labeling material 3 in order to easily detect the double strand-forming site 5.

In the method of detecting a target material according to the first exemplary embodiment, the first nucleic acid fragment 2 has a complementary base sequence capable of forming the double-stranded nucleic acid site with the aptamer 1. As the first nucleic acid fragment 2, for example, DNA, RNA, PNA, or the like can be used. In addition, the first nucleic acid fragment 2 may partially have a base sequence non-complementary to the aptamer 1, in addition to the base sequence complementary to the aptamer 1. By adding the non-complementary base sequence, this base sequence can be used as a spacer between the nucleic acid fragment and the substrate or between the labeling material 3 and the nucleic acid fragment, which can decrease steric hindrance. The double-stranded nucleic acid site between the first nucleic acid fragment 2 and the aptamer 1 may be positioned at any portion of the first nucleic acid fragment 2, for example, at an end or the center thereof. In addition, the first nucleic acid fragment 2 may be modified with the labeling material 3 in order to easily detect the double-stranded nucleic acid site.

In addition, it is preferable that a spacer be formed between the base sequence, which forms the double strand-forming site 5 between the aptamer 1 and the first nucleic acid fragment 2, and the substrate. That is, it is preferable that a first spacer be formed in the aptamer 1 and a second spacer be formed in the first nucleic acid fragment 2. These first and second spacers will be simply referred to as "spacer". In addition, the length of the first spacer may be the same as or different from that of the second spacer. It is preferable that this spacer be longer than or equal to 3 Å. As a result, the forming efficiency of the double-stranded nucleic acid site (double strand-forming site 5) can be inhibited from being decreased by steric hindrance or the like of the aptamer 1 and the first nucleic acid fragment 2. Further, it is more preferable that the spacer be shorter than or equal to 200 Å. As a result, a concentration effect obtained by fixing the aptamer and the nucleic acid fragment to the member surface to be adjacent to each other can be inhibited from deteriorating. It is more preferable that the spacer be longer than or equal to 10 Å and shorter than or equal to 50 Å. Such a spacer is not particularly limited as long as a bond can be formed between the aptamer and the nucleic acid fragment. As the spacer, nucleic acids having a non-complementary base sequence, or commonly-used linkers such as sugar chains, polypeptides, hydrocarbon chains, and oligoethylene glycols can be used. For example, the first spacer has a different base sequence from that of the second spacer, that is, does not have a complementary base sequence. In this case, the number of bases of the spacer is preferably less than or equal to 8 and more preferably less than or equal to 7. In the embodiment, the number of bases of the spacer is appropriately determined according to a detecting method. In an electrochemical measurement method, the number of bases of the spacer is more preferably less than or equal to 7. However, in a method other than the electrochemical measurement, the number of bases of the spacer may be more than or equal to 8 or may be more than or equal to 12.

In addition, an end of the aptamer 1 and an end of the first nucleic acid fragment 2 have a functional group for fixing them to the member by a chemical bond or a chemical adsorption. Such a functional group is not limited as long as a bond with the member which is not dissociated by a used solvent or pH conditions can be formed. As the functional group, commonly-used groups such as a carboxyl group, an amino group, a thiol group, a disulfide group, a succinimidyl group, a maleimide group, and biotin can be used. These functional groups can be synthesized using a commonly-used nucleic acid synthesis method, or groups formed by modifying nucleic acids of the functional groups with a commercially available linker or the like can be used. In addition, the functional group may modify any region as long as it does not inhibit a specific bond between an aptamer and a target material. For example, the functional group may modify an end or the center in the aptamer 1 or the first nucleic acid fragment 2. By forming the functional group at an end of the aptamer 1 or the first nucleic acid fragment 2, the design margin of the aptamer 1 can be improved.

In addition, by adjusting abundance ratios of the aptamer 1 and the first nucleic acid fragment 2 on the member surface, the forming efficiency and the stability of the double-stranded nucleic acid site can be changed, and response characteristics in the method of detecting a target material according to the first exemplary embodiment can be changed.

For example, when an abundance ratio of the nucleic acid fragment to the aptamer is increased, most parts of the aptamer on the member surface form the double-stranded nucleic acid site. In this case, a part of the aptamer in the single-stranded nucleic acid state is decreased. As a result, the target material efficiently binds the aptamer where the double-stranded nucleic acid site is formed, and the double-stranded nucleic acid site is cleaved. Therefore, even if the concentration of the target material is low, a high detection sensitivity can be obtained. On the other hand, when an abundance ratio of the aptamer to the nucleic acid fragment is increased, most parts of the nucleic acid fragment on the member surface form the double-stranded nucleic acid site. In this case, a part of the nucleic acid fragment in the single-stranded nucleic acid state is decreased. As a result, an S/N ratio can be improved when the cleavage of the double strand-forming site 5 is detected by the labeling material 3 which modifies the first nucleic acid fragment 2.

The above-described abundance ratios of the aptamer and the nucleic acid fragment on the member surface are not particularly limited and can be appropriately set according to the sequence of the aptamer, the ion strength or temperature of a measurement solution, and the like. However, in order not to excessively decrease the abundance ratio of the double-stranded nucleic acid site, it is preferable that a molar fraction aptamer/nucleic acid fragment be 0.05 to 20.

A material of the fixing member 4 according to the first exemplary embodiment is not particularly limited as long as the aptamer 1 and the first nucleic acid fragment 2 can be fixed thereto or a treatment for fixing the aptamer 1 and the first nucleic acid fragment 2 can be performed thereon. Examples of a method of fixing a nucleic acid to the member include a method of forming a peptide bond using a functional group of a nucleic acid and a functional group of the member surface; a method of chemical adsorbing a thiol group of a nucleic acid on the member surface in the presence of gold, platinum, silver, palladium, or the like; and a method of forming a biotin-avidin bond by fixing avidin to the member surface. In addition, a method, which is commonly used in a DNA chip or the like, of sequentially growing a nucleic acid using a functional group of the member surface may be used. When the member does not have such a functional group, a desired functional group may be formed by treating the member with thiol, a silane coupling agent, or the like. As the member, for example, a substrate, particles such as beads, or microchips may be used. The shape of the member is not particularly limited and may be, for example, planar or spherical. When the aptamer 1 and the first nucleic acid fragment 2 are fixed to the fixing member 4, the aptamer 1 and the first nucleic acid fragment 2 adjacent to each other forms the double strand-forming site 5 due to the complementary base sequence thereof, and thus the complex 11 is formed. In order to increase the forming ratio of the double-stranded nucleic acid site, an annealing treatment may be performed. Treatment conditions may be conditions commonly used for forming a double-stranded nucleic acid, or may be appropriately set based on the length, kind, ionic strength, and the like of complementary base pairs of a sequence to be used. In addition, the annealing treatment can be appropriately performed, for example, after each nucleic acid solution, a mixture thereof, or all the solutions are fixed to the member.

In addition, the fixing member 4 may be subjected to a blocking treatment after the aptamer 1 and the first nucleic acid fragment 2 are fixed thereto. By suppressing the adsorption of a material non-specific to the member surface through the blocking treatment, false-positive results can be reduced, and an S/N ratio can be improved. By controlling to aptamer 1 and the first nucleic acid fragment 2 to erect from the member in a substantially vertical direction, a binding ratio between the target material and the aptamer can be increased to obtain high sensitivity. For the blocking treatment, commonly-used blocking agents can be used, for example, hydrophilic macromolecules such as polyethylene glycol and acrylamide; proteins such as bovine serum albumin; sugar chains such as dextrin; lipids such as phosphatidylcholine; and hydrophilic thiols such as mercapto hexanol.

The method of detecting a target material according to the first exemplary embodiment is usually performed in a solution containing an inspection target. The solution described herein may be a commonly-used reaction solution. In addition, when each step is performed, conditions such as a temperature, a pH, and metal ions are appropriately set. However, in the method of detecting a target material according to the first exemplary embodiment, since a double strand portion of a nucleic acid is used, it is preferable that temperature conditions, pH, and the like be controlled such that a double strand bond of a nucleic acid can be held.

In the method of detecting a target material according to the first exemplary embodiment, a method of detecting the cleavage of the double strand-forming site 5 formed between the aptamer 1 and the first nucleic acid fragment 2 is not particularly limited. For example, a method of detecting physical and chemical changes of a nucleic acid and the labeling material 3 thereof caused by the cleavage of the double-stranded nucleic acid site can be used. The physical and chemical changes are not particularly limited, and color change, fluorescence change, permittivity change, electron transfer efficiency change, mass change, viscosity change, thermal change, and the like can be used. For example, by using the aptamer 1 labeled with a fluorescent material and the first nucleic acid fragment 2 labeled with a quencher, a increase in the distance between the fluorescent material and the quencher caused by the cleavage of the double-stranded nucleic acid site can be detected by the measurement of fluorescence resonance energy transfer (FRET), or a method of using a double-stranded nucleic acid indicator, such as SYBR (registered trademark) or Green I, which is intercalated into the double-stranded nucleic acid site and emits fluorescence. In addition, for example, a charge density change on the member surface, or a distance change or a contact frequency change between the labeling material 3 and the member surface caused by the cleavage of the double-stranded nucleic acid may be detected using a well-known method such as the measurement of surface plasmon resonance (SPR), surface acoustic wave (SAW), field-effect transistor (FET), or an electrochemical measurement.

The labeling material 3 according to the first exemplary embodiment is not particularly limited as long as it can amplify physical and chemical changes caused by the cleavage of the double strand-forming site 5, and examples thereof include fluorescent materials, quenchers, dielectrics, nucleic acids, electrochemical reactants, polar molecules, enzymes, catalysts, radioactive materials, proteins, and beads. A modifier for modifying a nucleic acid may not be provided when the cleavage of the double-stranded nucleic acid site is detected by the measurement of the weight of a nucleic acid or an electric permittivity change, for example, quartz crystal microbalance (QCM), FET, or SPR.

Here, an example of using an electrode reactant as the labeling material 3 to detect the cleavage of the double-stranded nucleic acid site will be described again using FIG. 6. In FIG. 6(*a*), a tip of the first nucleic acid fragment 2 is labeled with the labeling material 3. A terminal of the aptamer 1 and a terminal of the first nucleic acid fragment 2 are fixed to the fixing member 4, which is an electrode, thereby forming the complex 11. The base sequence of the aptamer 1 and the base sequence of the first nucleic acid fragment 2 are continuously complementary to each other such that the distance between the labeling material 3 and the fixing member 4 is not too short. The fixing member 4 is connected to an electrochemical measuring device along with a counter electrode and a reference electrode which are not illustrated in the drawing.

First, before the complex 11 is brought into contact with a solution of an inspection target, an electrochemical measurement is performed using the fixing member 4 as a working electrode. In this state, since the aptamer 1 and the first nucleic acid fragment 2 form the double strand-forming site 5, the labeling material 3 is positioned to be distant from the fixing member 4. As a result, the contact frequency of the labeling material 3 with the fixing member 4 is decreased. Therefore, when the labeling material 3 applies a potential to the fixing member 4 for oxidation and reduction, a low current value is observed.

Next, after the inspection target is brought into contact with the complex 11, an electrochemical measurement is performed using the fixing member 4 as a working electrode. When the inspection target contains the target material 7, the target material 7 binds to the double-stranded nucleic acid site of the aptamer 1 (FIG. 6(*b*), and the aptamer 1 is separated from the first nucleic acid fragment 2 (FIG. 6(*c*)). As a result, the contact frequency between the labeling material 3 and the fixing member 4 is recovered. As a result, the reaction current of the labeling material 3 is recovered. Accordingly, the reaction current of the labeling material 3 is increased when the target material 7 is in contact with the aptamer 1. When the inspection target does not contain the target material 7, the aptamer 1 continuously binds to the first nucleic acid fragment 2. Therefore, the reaction current of the labeling material 3 does not change.

Using the above-described method, whether or not the target material 7 exists can be inspected by comparing the reaction current values before and after the contact with the inspection target.

For example, when the reaction current before the contact with the inspection target is known in advance or is too small to be negligible, the measurement before the contact with the inspection target may not be performed.

In addition, between the steps or during each step, the member surface may be optionally washed.

In addition, in the first exemplary embodiment, a sensor chip including the above-described complex 11 can be used for detecting the target material 7. That is, this sensor chip includes the complex 11, and the complex 11 includes the aptamer 1 to which the target material 7 in a specimen specifically binds; the first nucleic acid fragment 2 that has a base sequence complementary to the aptamer 1; and the fixing member 4 to which a part of the aptamer 1 and a part of the first nucleic acid fragment 2 are fixed, in which the aptamer 1 has the double strand-forming site 5 capable of forming a double strand with the first nucleic acid fragment 2.

In addition, in the sensor chip, the double strand-forming site 5 which is formed by the aptamer 1 and the first nucleic acid fragment 2 may not contain a margin sequence. In addition, in the sensor chip, the double strand-forming site 5 may also be formed in a portion other than an end of the aptamer 1. In addition, as described below, the sensor chip includes a linking portion through which the aptamer 1 and the first nucleic acid fragment 2 are linked by a chemical bond or a chemical adsorption, and at least one portion of the linking portion may be fixed to the member by a chemical bond and a chemical adsorption. In this way, in the sensor chip, the complex 11 can appropriately adopt each configuration according to the embodiment.

In the sensor chip, the double strand-forming site 5 is cleaved by a bond between the target material 7 and the aptamer 1. As a result, the effects of the embodiment are obtained.

In addition, a device of detecting the target material 7 according to the first exemplary embodiment includes the above-described sensor chip; a binding portion that binds the target material 7 to the aptamer 1; and a detecting portion that detects the cleavage of the double strand. The binding portion brings an inspection target containing the target material 7 into contact with the complex 11. In other words, the binding portion may bring the sensor chip into contact with the target material 7. In addition, the detecting portion that detects the cleavage of the double-stranded nucleic acid site is not particularly limited as long as it can detect physical and chemical changes caused by the cleavage of the double-stranded nucleic acid site. For example, the detecting portion can detect changes in signals such as optical signals, electrical signals, and color signals. In this device of detecting a target material, by using the above-described method of detecting a target material, even if the concentration of the target material is low, a large signal change occurs, and thus a high detection sensitivity can be obtained. In addition, by using the sensor chip in which the aptamer is appropriately changed according to the detection target material, this device can be used for detecting various target materials.

Second Exemplary Embodiment

Figure 7:
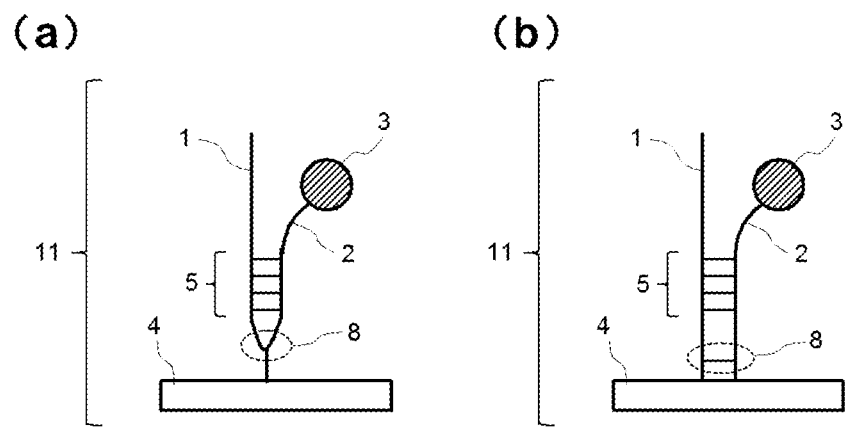
FIG. 7 is a diagram illustrating a configuration of a complex used for detecting a target material in a second exemplary embodiment.

In a second exemplary embodiment, the complex 11 includes a linking portion 8 through which a part of the aptamer 1 and a part of the first nucleic acid fragment 2 are linked to each other, and the linking portion 8 is fixed to the fixing member 4. For example, the aptamer 1 and the first nucleic acid fragment 2 are linked to each other by a chemical bond or a chemical adsorption. In addition, a part of the aptamer 1 and a part of the first nucleic acid fragment 2 may be linked to a linker molecule. Hereinafter, the second exemplary embodiment will be described. FIG. 7 is a diagram illustrating the complex 11 according to the second exemplary embodiment.

Since the second exemplary embodiment is an application example of the first exemplary embodiment, the description of the same points as those of the first exemplary embodiment will not be repeated.

The complex 11 according to the second exemplary embodiment includes the linking portion 8 through which the aptamer 1 and the first nucleic acid fragment 2 bind to each other by a chemical bond or a chemical adsorption, and at least one portion of the linking portion 8 is fixed to the fixing member 4 by a chemical bond or a chemical adsorption.

In the second exemplary embodiment, by the aptamer 1 and the first nucleic acid fragment 2 being linked to each other, the fixed state of the aptamer 1 and the first nucleic acid fragment 2 on the surface of the fixing member 4 can be accurately controlled. As a result, background values of a measured value are reduced, and a variation of a sensor chip is reduced, which improves the measurement reliability and the detection sensitivity.

The effects and operations of the second exemplary embodiment will be described in detail using FIG. 7(a).

First, the complex 11 is prepared. The aptamer 1 and the first nucleic acid fragment 2 are linked to each other by a chemical bond or a chemical adsorption other than a hydrogen bond forming a double strand, thereby forming the linking portion 8. In this embodiment, the linking portion 8 refers to a portion through which the aptamer 1 and the first nucleic acid fragment 2 are linked. Next, the linking portion 8 is fixed to the fixing member 4 by a chemical bond or a chemical adsorption other than a hydrogen bond forming a double strand. The aptamer 1 and the first nucleic acid fragment 2 fixed to the fixing member 4 form the double strand-forming site 5 through a complementary base sequence, thereby forming the complex 11.

Similarly to the method according to the first exemplary embodiment, the complex 11 prepared as above can be used for detecting a target material by using whether or not the cleavage of the double-stranded nucleic acid site exists as an index.

Here, the aptamer 1 and the first nucleic acid fragment 2 are linked to each other and then are fixed to the member such that the aptamer 1 and the first nucleic acid fragment 2 are fixed to be adjacent to each other. As a result, the double strand-forming site 5 is efficiently formed. Therefore, in the method of detecting a target material according to the second exemplary embodiment, background values are reduced, and the measurement sensitivity is improved.

In addition, the nucleic acid fragment and the aptamer are uniformly dispersed on and fixed to the member surface. Therefore, in a sensor chip according to the second exemplary embodiment, a variation during manufacturing is reduced, and yield is improved.

In addition, the abundance ratios of the aptamer 1 and the first nucleic acid fragment 2 on the member surface are equal to the contents of nucleic acids on the linking portion of the aptamer and the nucleic acid fragment, respectively. Therefore, the abundance ratios can be accurately controlled by studying manufacturing conditions of the linking portion. As a result, in the method of detecting a target material according to the second exemplary embodiment, it is easy to control the forming efficiency and stability of the double-stranded nucleic acid site, and the detection sensitivity can be improved.

In the second exemplary embodiment, the same materials as those of the first exemplary embodiment can be used for the aptamer 1 and the first nucleic acid fragment 2. However, functional groups of the aptamer 1 and the first nucleic acid fragment 2 are appropriately used such that the linking portion 8 can be formed. In addition, the formation of a link is not particularly limited, and a commonly-used chemical reaction can be used. It is preferable that the linking portion 8 has a functional group for forming a chemical bond or a chemical adsorption with the fixing member 4. Examples of such a linking method include a method of binding the aptamer 1 and the first nucleic acid fragment 2 to two functional groups of a linker molecule having different three functional groups and then fixing the remaining one functional group to the member. In addition, a nucleic acid in which, for example, a modified base containing a functional group for binding to the member and a linker molecule are inserted between the aptamer sequence and the nucleic acid fragment may be synthesized by a commonly-used nucleic acid synthesis method. Such a linker is not particularly limited, and various commercially available reagents can be used, for example, Dithiol Phosphoramidite (manufactured by Glen research).

In the second exemplary embodiment, the same material as that of the first exemplary embodiment can be used for the fixing member 4. It is preferable that the fixing member 4 optionally have a functional group for fixing the linking portion 8.

In FIG. 7(a), the aptamer 1 and the first nucleic acid fragment 2 linked to each other are fixed to the member at one position through the linking portion 8. However, the linking portion 8 may be fixed to the member at multiple positions.

In addition, when a linker molecule is used in the linking portion 8, a structure thereof is not limited to a triple-branched structure as illustrated in FIG. 7(a), and linker molecules having various chemical structures can be used. For example, as illustrated in FIG. 7(b), a ladder-shaped structure may be used, or a linking ratio of the aptamer and the nucleic acid fragment may not be 1:1 using a multi-branched linker molecule.

In addition, the length of the linker molecule is not particularly limited. However, the length is preferably greater than or equal to 3 Å such that the forming efficiency of the double-stranded nucleic acid site is inhibited from being decreased by steric hindrance of the aptamer and the nucleic acid fragment; and is preferably less than or equal to 200 Å such that a concentration effect obtained by fixing the aptamer and the nucleic acid fragment to the member surface to be adjacent to each other is inhibited from deteriorating.

Third Exemplary Embodiment

Figure 8:
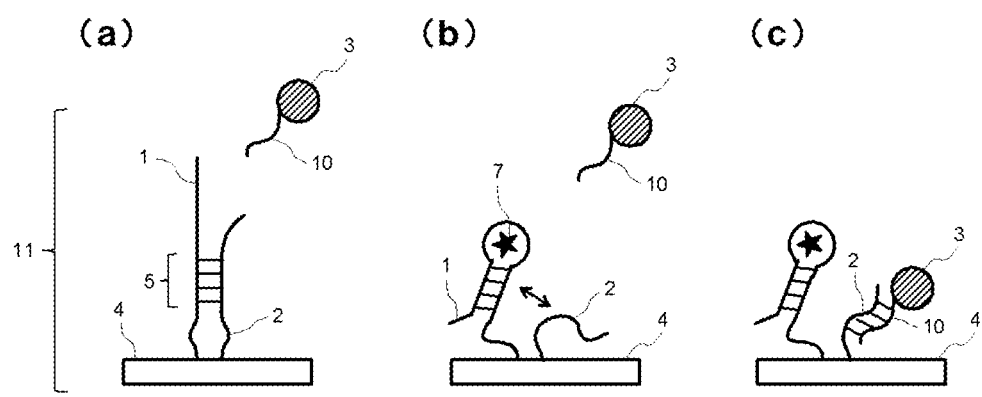
FIG. 8 is a diagram illustrating the procedure of a method of detecting a target material according to a third exemplary embodiment.

Since a third exemplary embodiment is an application example of the first and second exemplary embodiments, the description of the same points as those of the first and second exemplary embodiments will not be repeated. FIG. 8 is a diagram illustrating the procedure of a method of detecting a target material according to the third exemplary embodiment. The third exemplary embodiment is the same as the first and second exemplary embodiments, in that the aptamer 1 and the first nucleic acid fragment 2 are fixed to the fixing member 4, and the aptamer 1 and the first nucleic acid fragment 2 form the double strand-forming site 5. However, the cleavage of the double-stranded nucleic site caused by the target material 7 is detected using a second nucleic acid fragment 10. That is, in the method of detecting a target material according to the third exemplary embodiment, the step of detecting the cleavage of the double strand includes: a step of binding the second nucleic acid fragment 10, which has a base sequence complementary to the first nucleic acid fragment 2, to the first nucleic acid fragment 2 which is separated from the double strand-forming site 5; and a step of detecting a bond between the first nucleic acid fragment 2 and the second nucleic acid fragment 10 to detect the cleavage of the double strand.

Hereinafter, the method of detecting a target material according to the third exemplary embodiment will be described using FIG. 8.

First, similarly to the first and second exemplary embodiments, the complex 11 is prepared. The aptamer 1 and the first nucleic acid fragment 2 in the complex form the double-stranded nucleic acid site through a complementary base sequence (FIG. 8(*a*)).

In the third exemplary embodiment, the second nucleic acid fragment 10, which has abase sequence capable of forming a bond through a base sequence complementary to the first nucleic acid fragment 2 in advance, is added to a measurement solution. The second nucleic acid fragment 10 is modified with the labeling material 3 in advance.

Next, the complex 11 is brought into contact with an inspection target. When the inspection target contains the target material 7, the target material 7 binds to the aptamer 1. As a result, the double strand-forming site 5 is cleaved (FIG. 8(*b*)).

Next, the second nucleic acid fragment 10 binds to the first nucleic acid fragment 2 (FIG. 8(*c*)). Before the aptamer 1 binds to the target material 7, the first nucleic acid fragment 2 forms the double strand-forming site 5 with the aptamer 1 fixed to the same fixing member 4. That is, the first nucleic acid fragment 2 and the aptamer 1 exist in a state of being locally concentrated on the member surface. As a result, an apparent binding constant of the double strand-forming site 5 is high. Therefore, the second nucleic acid fragment 10 which exists in the solution is stronger in a competition reaction with the aptamer 1, cannot dissociate the double strand-forming site 5, and does not bind to the first nucleic acid fragment 2. On the other hand, when the aptamer 1 binds to the target material 7, the double strand-forming site 5 is cleaved, and a binding strength between the aptamer 1 and the first nucleic acid fragment 2 is lost. Therefore, the second nucleic acid fragment 10 can form complementary base pairs with the first nucleic acid fragment 2.

Next, the second nucleic acid fragment 10 binding to the first nucleic acid fragment 2 is detected. In this case, the detection of the second nucleic acid fragment 10 binding to the first nucleic acid fragment 2 is not limited as long as physical and chemical changes caused by the labeling material 3 of the second nucleic acid fragment 10 which binds to the fixing member 4 through the first nucleic acid fragment 2 can be detected. For example, the detection refers to the detection of changes in signals such as optical signals, electrical signals, and color signals.

In the third exemplary embodiment, when an inspection target does not contain a material binding to the aptamer 1, a bond between the aptamer 1 and the first nucleic acid fragment 2 is not cleaved. Therefore, the second nucleic acid fragment 10 does not bind to the first nucleic acid fragment 2. Accordingly, by detecting the second nucleic acid fragment 10 binding to the first nucleic acid fragment 2, whether or not the inspection target contains the target material 7 can be detected.

In the third exemplary embodiment, when the labeling material 3 is not present on and does not bind to the fixing member 4, a background level is low, and thus a high S/N ratio is obtained. As a result, according to the third exemplary embodiment, the target material can be detected with high sensitivity.

In FIG. 8(*a*), the second nucleic acid fragment 10 is added before the contact between the inspection target and the complex 11. However, the second nucleic acid fragment only needs to exist when the cleavage between the aptamer 1 and the first nucleic acid fragment 2 occurs, and the addition timing thereof is not limited.

It is particularly preferable that the second nucleic acid fragment 10 exists in a measurement solution when the target material 7 is in contact with the complex 11. As a result, the first nucleic acid fragment 2 in the single-stranded state formed by the cleavage of the double strand-forming site 5 of the complex 11 rapidly binds to the second nucleic acid fragment 10. As a result, even if the aptamer 1 separated from the first nucleic acid fragment 2 emits the target material 7 according to an equilibrium reaction to be in the single-stranded state, the rebinding thereof to the first nucleic acid fragment 2 is inhibited. Accordingly, even if the concentration of the target material 7 is low, the dissociation between the aptamer 1 and the first nucleic acid fragment 2 advances, and a large signal can be obtained.

In the third exemplary embodiment, the second nucleic acid fragment 10 has a complementary base sequence capable of forming the double-stranded nucleic acid site with the first nucleic acid fragment 2. As the second nucleic acid fragment 10, for example, DNA, RNA, PNA, or the like can be used. In addition, the second nucleic acid fragment 10 may partially have a base sequence non-complementary to the first nucleic acid fragment 2, in addition to the base sequence complementary to the first nucleic acid fragment 2. The double-stranded nucleic acid site between the second nucleic acid fragment 10 and the first nucleic acid fragment 2 may be positioned at any portion of the second nucleic acid fragment 10, for example, at an end or the center thereof. In addition, in order to promote the detection of a bond with the first nucleic acid fragment 2 described below, the second nucleic acid fragment 10 may be modified with the labeling material 3 such as fluorescent materials, quenchers, electrochemical reactants, polar molecules, enzymes, and catalysts.

In addition, in the third exemplary embodiment, the number of complementary bases between the second nucleic acid fragment 10 and the first nucleic acid fragment 2 depends on the strength of the bond between the aptamer 1 and the first nucleic acid fragment 2, and an optimum value thereof is appropriately used. That is, in the absence of the target material, the number of bases is controlled not to be excessive such that a binding strength between the aptamer 1 and the first nucleic acid fragment 2 is weak to the extent that a bond thereof is not separated. In the presence of the target material, the number of bases is controlled to be large to the extent that the second nucleic acid fragment 10 stably binds to the first nucleic acid fragment 2 in a solution. The specific number of bases varies depending on the base sequences and ionic strengths of the aptamer 1 and the first nucleic acid fragment 2. However, the number of complementary bases is more than or equal to 8 bases as a reference value capable of stably forming a bond in a solution, and is preferably more than or equal to the number of complementary bases between the aptamer 1 and the first nucleic acid fragment 2 and is more preferably more than or equal to 2 bases. In addition, in the absence of the target material, it is preferable that the number of complementary bases which is surplus to the number of complementary bases between the aptamer 1 and the first nucleic acid fragment 2 be less than or equal to 10 bases as a reference value in which a bond between the aptamer 1 and the first nucleic acid fragment 2 is not separated.

Fourth Exemplary Embodiment

In a fourth exemplary embodiment, a case where the aptamer 1 and the first nucleic acid fragment 2 are fixed to the same solvophilic member by a chemical bond and a chemical adsorption will be described. This embodiment is an application example of the first to third exemplary embodiments, and the description of the same points thereof will not be repeated.

That is, in this embodiment, the fixing member 4 has a solvophilic region (supplementary portion 14) in a different region from a fixing region (detecting portion 13) where the aptamer 1 and the first nucleic acid fragment 2 are fixed. Due to its high affinity to a solvent, the supplementary portion 14 can supplement the second nucleic acid fragment 10 contained in the solvent by the second nucleic acid fragment 10 permeating a surface of the supplementary portion 14. The second nucleic acid fragment 10 supplemented with the supplementary portion 14 moves on the surface of the supplementary portion 14 and can easily bind to the first nucleic acid fragment 2 fixed to the detecting portion 13.

FIG. 9 is a diagram illustrating the procedure of the method of detecting a target material according to the fourth exemplary embodiment. In the fourth exemplary embodiment, the aptamer 1 and the first nucleic acid fragment 2 are fixed to a part of the fixing member 4. In the fourth exemplary embodiment, the entire portion of the fixing member 4 is solvophilic, but the fourth exemplary embodiment is not limited to this configuration. Only a part of the supplementary portion 14 may be solvophilic, or a part or the entire portion of a surface of any member may be treated to be solvophilic. In addition, in order to detect the cleavage of the double-stranded nucleic acid site between the aptamer and the nucleic acid fragment caused by the target material 7, similarly to the third exemplary embodiment, the second nucleic acid fragment 10 modified with the labeling material 3 in advance is used. Hereinafter, a portion of the solvophilic fixing member 4 where nucleic acids such as the aptamer and the nucleic acid fragment are fixed will be referred to as "detecting portion 13".

The method of detecting a target material according to the fourth exemplary embodiment will be described using FIG. 9.

First, the aptamer 1 and the first nucleic acid fragment 2 are fixed to the detecting portion 13 of the fixing member 4 by a chemical bond and a chemical adsorption. The aptamer 1 and the first nucleic acid fragment 2 fixed to the detecting portion 13 form the double strand-forming site 5 through a complementary base sequence (FIG. 9(a)).

Next, a measurement solution containing the target material 7 and the second nucleic acid fragment 10 is brought into contact with a portion (supplementary portion 14) of the fixing member 4 other than the detecting portion 13. When the measurement solution is in contact with the solvophilic member, the target material 7 and the second nucleic acid fragment 10 permeates the member (FIG. 9(b)) along with the solution.

Next, the aptamer 1 and the target material 7 in the detecting portion 13 bind to each other. When the permeation of the solution which is described above in the previous step reaches the detecting portion 13, the target material 7 in the solution comes into contact with the aptamer 1. As a result, the aptamer 1 and the target material 7 bind to each other, and the double-stranded nucleic site between the aptamer 1 and the first nucleic acid fragment 2 is cleaved (FIG. 9(c)).

Next, the second nucleic acid fragment 10 binds to the first nucleic acid fragment 2 of the detecting portion 13 (FIG. 9(d)). Since the aptamer 1 fixed to the member in the previous step binds to the target material 7, a binding strength between the aptamer 1 and the first nucleic acid fragment 2 is lost. Therefore, the second nucleic acid fragment 10 can form complementary base pairs with the first nucleic acid fragment 2.

Next, the target material is detected by measuring physical and chemical changes of the detecting portion 13 caused by the labeling material 3 of the second nucleic acid fragment 10 binding to the fixing member 4 through the first nucleic acid fragment 2. When an inspection target contains the target material, the first nucleic acid fragment 2 and the second nucleic acid fragment 10 form complementary base pairs to bind to each other through the above-described steps. On the other hand, when an inspection target does not contain the target material, the double strand-forming site 5 formed by the aptamer 1 and the first nucleic acid fragment 2 is not eliminated. As a result, the second nucleic acid fragment 10 does not bind to the first nucleic acid fragment 2. Accordingly, whether or not an inspection target contains the target material can be determined by measuring physical and chemical changes of the detecting portion 13 caused by the labeling material 3 of the second nucleic acid fragment 10 binding to the fixing member 4 through the first nucleic acid fragment 2.

According to the fourth exemplary embodiment, a specimen in contact with the solvophilic member spontaneously permeates the member, and the inspection advances. Therefore, the handling of the specimen is simple, and the inspection of the target material is easily performed.

As the method of detecting a target material in which an aptamer is fixed to a solvophilic member, a lateral flow method is reported in Non-Patent Document 6. In the reported method of the related art, a target material is detected by forming a so-called sandwich structure where an aptamer fixed to a member binds to a labeled aptamer. Therefore, it is necessary that at least two or more aptamers for recognizing different epitopes of a target material be prepared, and time and effort are required for obtaining the aptamers. On the other hand, in the method according to the fourth exemplary embodiment, if one aptamer is prepared, the target material can be detected, and time and efforts for obtaining the aptamer are saved.

The solvophilic member who is used in the fourth exemplary embodiment is not particularly limited as long as it is a member which is permeated by the measurement solution in contact therewith. However it is preferable that a material having a contact angle of less than 90° with a specimen or a solvent for diluting a specimen be used. In addition, it is preferable the member is porous for the following reasons. For example, the permeation of the solution is promoted by a capillary phenomenon, or the fixing amount of an aptamer is increased to increase a signal change during the binding of the target material. As a result, effects of reducing the time required for the detection and increasing the detection sensitivity are obtained. Examples of such a porous member include porous filters of glass fibers, nitrocelluloses, celluloses, synthetic fibers, non-woven fabrics, and the like. In addition, another solvophilic member which is not illustrated in FIG. 9 may be laminated on or linked to the solvophilic fixing member 4 to which the aptamer and the nucleic acid fragment are fixed. As a result, there are advantageous effects in that, for example, impurities contained in a specimen can be removed by combining members having different solvophilicities and porosities; and for example, when the second nucleic acid fragment described below permeates a member in advance, a member containing the second nucleic acid fragment and a member containing the detecting portion can be separately prepared, and the manufacturing thereof is simple.

In the fourth exemplary embodiment, as a method of chemical binding and chemically adsorbing the aptamer and the nucleic acid fragment to the solvophilic member, the same method as those of the first to third exemplary embodiments using a functional group may be used. A method of fixing the aptamer 1 and the first nucleic acid fragment 2 to the detecting portion 13 is not particularly limited. For example, a part of the member may be subjected to masking, or when the solution containing the aptamer 1 and the first nucleic acid fragment 2 is caused to react with the member, a reaction solution may be spotted to cause a fixing reaction on only a part of the solvophilic fixing member 4.

In the fourth exemplary embodiment, the measurement of physical and chemical changes of the detecting portion 13 is not limited as long as physical and chemical changes caused by the presence of the labeling material 3 in the detecting portion 13 can be measured. For example, the measurement refers to the measurement of changes in signals such as optical signals, electrical signals, and color signals.

In addition, in the fourth exemplary embodiment, the labeling material 3 is not particularly limited. For example, chromogenic materials, electrochemical reactants, and catalyst materials can be used. When a chromogenic material is used, and when the second nucleic acid fragment 10 binds to the nucleic acid fragment, the color of the detecting portion changes, and thus the inspection results can be easily determined by visual inspection or a simple image sensor. Examples of such a chromogenic material include dyes, coloring beads, and metal fine particles, such as gold nanoparticles, formed in a surface plasmon. In addition, when an electrochemical reactants is used, a bond between the second nucleic acid fragment and the nucleic acid fragment can be detected as a current change by providing a conductive material near the detecting portion and using the conductive material as a working electrode of an electrochemical reaction, and the inspection results can be converted into electrical signals using a simple device. Examples of such an electrochemical reactant include metals, metal complexes, quinones and derivatives thereof, methylene blues and derivatives thereof, and heterocyclic compounds such as pyrroles, pyridines, and viologens. In addition, when a catalyst material is used, changes in the color or electrochemical reaction characteristics of the detecting portion can be caused by a combination of the used catalyst material with a substrate or an electron transfer mediator. When a catalyst is used, if the second nucleic acid fragment 10 binds to the first nucleic acid fragment 2, a reaction causing the changes in the color or electrochemical reaction characteristics of the detecting portion 13 is continuously caused, and signals are amplified. Therefore, the target material can be detected with high sensitivity. Examples of such a catalyst material which can be used include oxidases such as glucose oxidase and bilirubin oxidase; dehydrogenases such as glucose dehydrogenase; coenzyme oxidases such as diaphorase; peroxide reductases such as horseradish peroxidase and catalase; metal catalysts such as Pt and titanium oxide; catalytic nucleic acids such as ribozyme and deoxyribozyme; and aptamers, such as hemin aptamer, having a binding ability to a catalyst active material. When the electron transfer mediator and the substrate can be appropriately selected according to the kind of the used enzyme or catalyst. These labeling materials can easily modify the nucleic acid fragment using a commonly-used reaction such as amine coupling, a gold-thiol reaction, or a nucleic acid elongation reaction.

In FIG. 9, the measurement solution containing the target material 7 and the second nucleic acid fragment 10 is in contact with the solvophilic fixing member 4 in FIG. 9(b). However, in order to detect the target material in the fourth exemplary embodiment, the second nucleic acid fragment 10 only need to exist in the measurement solution when the target material 7 is in contact with the aptamer 1. For example, the second nucleic acid fragment 10 may be caused to permeate the solvophilic member in advance, or after a specimen and a solution containing the second nucleic acid fragment 10 are mixed in advance, the mixture may be brought into contact with the solvophilic member.

Fifth Exemplary Embodiment

Figure 10:
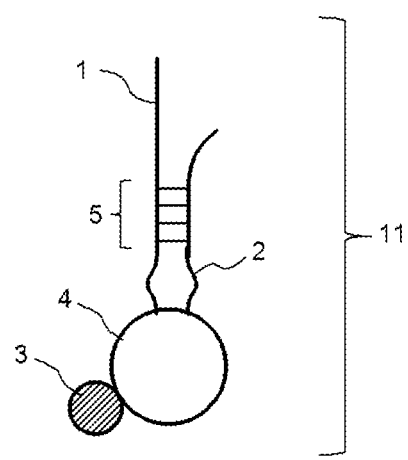
FIG. 10 is a diagram illustrating a configuration of a complex used for detecting a target material in a fifth exemplary embodiment.

In a fifth exemplary embodiment, a case where the second nucleic acid fragment 10 is fixed to a solvophilic member (member 21) will be described using FIGS. 10 and 11. That is, in this embodiment, the step of binding the second nucleic acid fragment 10 includes a step of binding the second nucleic acid fragment 10, which is fixed to a substrate (member 21), to the first nucleic acid fragment 2 which is separated from the double strand-forming site 5. This substrate (member 21) has a solvophilic region (supplementary portion 14) in a different region from a fixing region (detecting portion 13) where the second nucleic acid fragment 10 is fixed. This embodiment is an application example of the first to fourth exemplary embodiments, and the description of the same points thereof will not be repeated.

FIG. 11 is a diagram illustrating the procedure of a method of detecting a target material according to the fifth exemplary embodiment. A device (FIG. 11(a)) of detecting a target material according to the fifth exemplary embodiment includes a sample introducing portion 15, a complex holding portion 16, and a member 21. The sample introducing portion 15 is a solvophilic member. The complex holding portion 16 is a solvophilic member which is permeated by the complex 11 in advance. The member 21 is a solvophilic member in which the second nucleic acid fragment 10 is fixed into the detecting portion 13. As illustrated in FIG. 10, the complex 11 according to the fifth exemplary embodiment has the following configuration. That is, the aptamer 1 and the first nucleic acid fragment 2 are fixed to the same fixing member 4 by a chemical bond and a chemical adsorption. The fixing member 4 is fine particles such as a microsphere or a microfiber. The fixing member 4 is modified with the labeling material 3. The aptamer 1 and the first nucleic acid fragment 2 form the double strand-forming site 5 through a complementary base sequence.

The method of detecting a target material according to the fifth exemplary embodiment will be described using FIG. 11.

First, an inspection target containing the target material 7 is poured into the sample introducing portion 15. A solution of the inspection target permeates the sample introducing portion 15 and then permeates the complex holding portion 16. The sample introducing portion 15 is in contact with the complex holding portion 16. Along with the permeation of the measurement solution, the target material 7 contained in the solution permeates the complex holding portion 16 (FIG. 11(b)).

Next, the solution is further immersed and permeates the member 21. At this time, the complex 11 of the complex holding portion 16 is eluted into the measurement solution. The complex 11 permeates the member 21 along with the solution and the target material 7. At the same time, the target material 7 binds to the aptamer 1 of the complex 11. Next, the double strand-forming site 5 between the aptamer 1 and the first nucleic acid fragment 2 is cleaved.

Next, the permeation of the solution further advances, and the complex 11 in which the double-stranded nucleic acid site is cleaved reaches the detecting portion 13. As a result, the first nucleic acid fragment 2 and the second nucleic acid fragment 10 which have yet to form the double-stranded nucleic acid site form the double-stranded nucleic acid site, and the complex 11 binds to the detecting portion 13.

Next, the target material is detected by detecting the labeling material 3 which exists in the detecting portion 13. When an inspection target material contains the target material, the complex 11 containing the labeling material 3 binds to the detecting portion 13 through the above-described step, and thus the labeling material 3 exists in the detecting portion 13. On the other hand, when an inspection target does not contain the target material, the double strand-forming site 5 formed by the aptamer 1 and the first nucleic acid fragment 2 is not eliminated. As a result, since the complex 11 does not bind to the detecting portion 13, the labeling material 3 does not exist in the detecting portion 13. Accordingly, whether or not an inspection target contains the target material can be determined by measuring physical and chemical changes of the detecting portion 13 caused by the labeling material 3.

In this way, even if the second nucleic acid fragment 10 is fixed to the detecting portion of the solvophilic member, the target material can be detected.

That is, in this embodiment, the aptamer 1 and the first nucleic acid fragment 2, or the second nucleic acid fragment 10 is fixed to the detecting portion of the solvophilic member (the fixing member 4 or the member 21). The cleavage of a double strand between the aptamer 1 and the first nucleic acid fragment 2 can be detected by detecting a bond between the first nucleic acid fragment 2 and the second nucleic acid fragment 10 in the detecting portion of the member.

In this embodiment, the fixing member 4 is not particularly limited as long as it is fine particles having dispersibility in a solvent of the solution poured into the sample introducing portion. For example, commonly-used materials such as gold nanoparticles, latex beads, and resin beads can be used. As in the case of metal particles which develop a color by surface plasmon absorption or colored beads, when the fine particles cause physical and chemical changes of the detecting portion with their inherent characteristics, the labeling material may not be provided.

As a modifier according to the fifth exemplary embodiment, the same material as that of the fourth exemplary embodiment can be used. In addition, in FIG. 10, the labeling material 3 modifies the fixing member 4 which is fine particles. However, the labeling material 3 may modify the nucleic acid fragment or the aptamer as long as it does not inhibit a bond between the aptamer and the target material or a bond between the first nucleic acid fragment and the second nucleic acid fragment.

As the sample introducing portion, the complex holding material, and the solvophilic member according to the fifth exemplary embodiment, the same material as the solvophilic member described in the fourth exemplary embodiment can be used. In addition, in FIG. 10, the sample introducing portion and the complex holding portion are approximately horizontally arranged, but are not limited thereto. The respectively portions may be laminated.

Sixth Exemplary Embodiment

In a sixth exemplary embodiment, a method of detecting a target material will be described, in which a binding strength of a double strand between the aptamer and the first nucleic acid fragment dynamically changes during the target material detecting step. That is, the step of detecting a target material according to this embodiment includes: a cleavage energy applying step of weakening a binding strength of a double strand between the aptamer and the first nucleic acid fragment; and a double strand stabilizing step of strengthening a binding strength of a double strand between the aptamer and the first nucleic acid fragment.

The sixth exemplary embodiment will be described in detail using FIGS. 12 and 13. The sixth exemplary embodiment is an application example of the first to fifth exemplary embodiments, and the description of the same points thereof will not be repeated.

Figure 12:
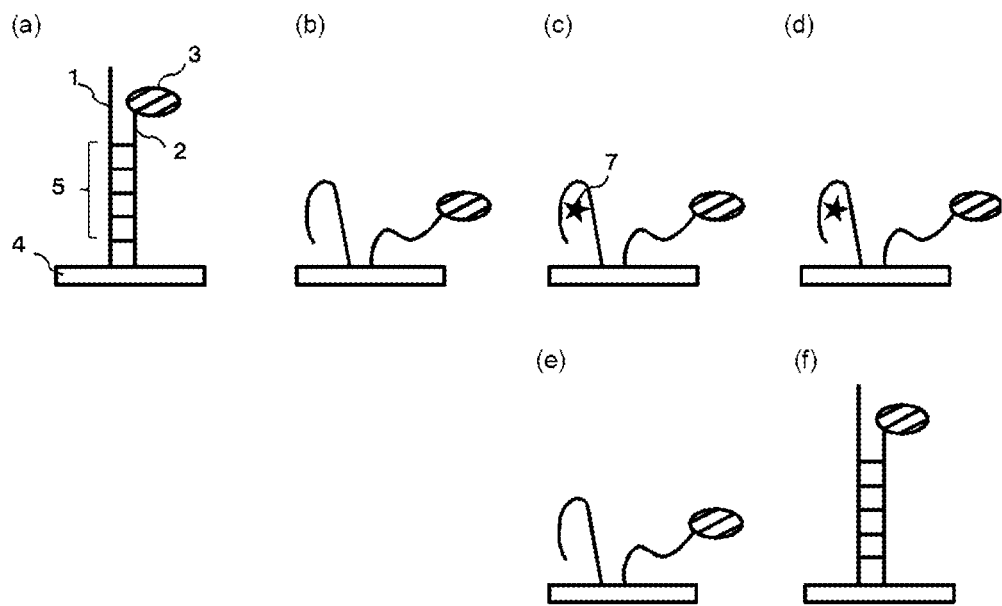
FIG. 12 is a diagram illustrating the procedure of a method of detecting a target material according to a sixth exemplary embodiment.
Figure 13:
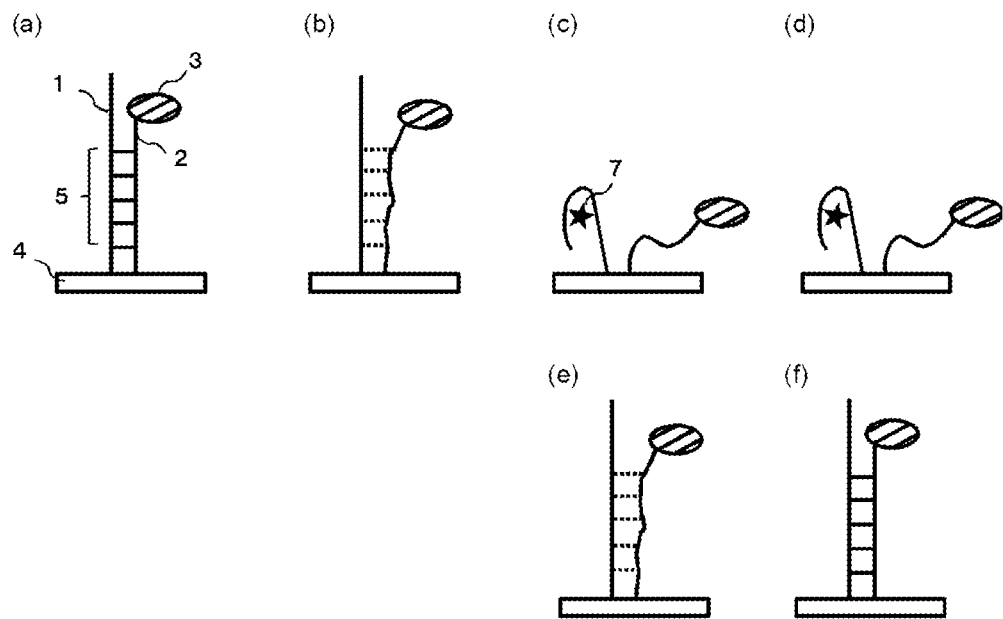
FIG. 13 is a diagram illustrating the procedure of the method of detecting a target material according to the sixth exemplary embodiment.

FIG. 12 is a diagram illustrating the target material detecting step when an energy which is higher than or equal to a binding energy between the aptamer and the first nucleic acid fragment is applied in the cleavage energy applying step.

First, through the same complex preparing step as those of the first to fifth exemplary embodiments, the complex 11 in which the aptamer 1 and the first nucleic acid fragment 2 are fixed to the fixing member 4 is formed (FIG. 12(a)).

Next, through the cleavage energy applying step, a double-stranded bond of the complex 11 between the aptamer 1 and the first nucleic acid fragment 2 is weakened. Since the applied cleavage energy is higher than or equal to the binding energy between the aptamer 1 and the first nucleic acid fragment 2, the aptamer 1 and the first nucleic acid fragment 2 cannot hold the double-stranded state and are cleaved. At this time, the aptamer 1 and the first nucleic acid fragment 2 are fixed to the fixing member 4, and thus exist on the member surface in the single-stranded state (FIG. 12(b)).

Next, the target material 7 binds to the aptamer 1. When a specimen contains the target material, the target material 7 can easily bind to the aptamer in the single-stranded state (FIG. 12(c)). On the other hand, when a specimen does not contain the target material, the aptamer is held in the single-stranded state (FIG. 12(e)).

Next, through the double strand stabilizing step, a bond between the aptamer 1 and the first nucleic acid fragment 2 is strengthened. Here, when a specimen contains the target material 7, the target material 7 already binds to the aptamer 1 in the previous steps. Therefore, the formation of a double-stranded bond by the aptamer 1 and the first nucleic acid fragment 2 is inhibited (FIG. 12(d)). On the other hand, when a specimen does not contain the target material, the aptamer 1 in the single-stranded state and the first nucleic acid fragment 2 rebind to each other to form a double strand (FIG. 12(f)).

Next, through the step of detecting the cleavage of the double strand, the target material is detected. That is, the double strand is cleaved (FIG. 12(d)) in the presence of the target material and is not cleaved in the absence of the target material (FIG. 12(f)). In this way, the presence and absence of the target material can be distinguished from each other by using the existence of the cleavage of the double strand as an index.

According to this embodiment, a binding strength of a double strand between the aptamer and the first nucleic acid fragment is dynamically changed during the target material detecting step. As a result, the detection accuracy of the target material and the reliability are improved. That is, by weakening a binding strength of a double strand in the stage of binding the aptamer to the target material, a double-strand holding ability is suppressed, and a double-strand cleaving ability is improved. As a result, in the presence of the target material, a double strand between the aptamer and the first nucleic acid fragment is dissociated, and the aptamer binds to the target material. Accordingly, even if the concentration of the target material is low, the cleavage of a double strand is likely to occur, and the detection sensitivity of the target material is improved.

In addition, by strengthening a binding strength of a double strand in the double strand cleavage detecting step, a double-strand holding ability is improved, and a double-strand cleaving ability is suppressed. As a result, the aptamer and the nucleic acid fragment which are dissociated by the application of a cleavage energy rapidly rebind to each other to form a double strand in the absence of the target material. Accordingly, the dissociation of a double strand in the absence of the target material is suppressed, and the detection reliability is increased. In this way, according to this embodiment, the superior method of detecting a target material in which both the detection sensitivity and the reliability are simultaneously improved is provided.

In this case, the complex 11 (FIG. 13(a)) formed in the complex preparing step is in the double-stranded state in which a binding energy is weakened by being applied with a cleavage energy (FIG. 13(b)). In a double strand in which a binding energy is weakened, a double-strand holding ability is weakened, an double-strand cleaving ability is increased. Therefore, when the target material 7 exists in a specimen, the aptamer 1 and the target material 7 easily bind to each other. Therefore, the double strand is cleaved (FIG. 13(c)). The aptamer 1 binding to the target material 7 holds the cleavage state after the double strand stabilizing step (FIG. 13(d)). On the other hand, when the target material 7 does not exist in a specimen, the aptamer holds the unstable double-stranded state (FIG. 13(e)) and returns to the stable double-stranded state through the subsequent double strand stabilizing step (FIG. 13(f)).

In this way, even if the applied cleavage energy is lower than a binding energy between the aptamer and the first nucleic acid fragment, in the presence of the target material, an effect of promoting a bond between the aptamer and the target material can be obtained; and in the absence of the target material, an effect of suppressing the dissociation of a double-strand can be obtained.

In this embodiment, the application of a cleavage energy refers to any means for weakening a binding strength based on a complementary base sequence formed between the aptamer and the first nucleic acid fragment, and this means is not particularly limited. Examples of such means include various operations in a measurement solution such as an increase in temperature, an increase in pH, a decrease in ionic strength, or an increase in organic solvent concentration; and the exchange of the measurement solution with such a liquid. The application of a cleavage energy is performed before or during the step of binding the target material to the aptamer.

In addition, in this embodiment, the double strand stabilizing step refers to any means for strengthening a binding strength based on a complementary base sequence formed between the aptamer and the first nucleic acid fragment, and this means is not particularly limited. Examples of such means include various operations in a measurement solution such as a decrease in temperature, the neutralization of pH, an increase in ionic strength, or a decrease in organic solvent concentration; and the exchange of the measurement solution with such a liquid. The double strand stabilizing step is performed after the step of binding the target material to the aptamer and before or during the step of detecting the step of detecting the cleavage of the double strand.

In the method of detecting a target material according to this embodiment in which a binding strength of a double strand between the aptamer and the first nucleic acid fragment dynamically changes, both the aptamer and the first nucleic acid fragment are fixed to the fixing member, and thus a particularly significant effect is exhibited. When both the aptamer and the first nucleic acid fragment are fixed to the fixing member, a double-strand holding ability is suppressed by the application of a cleavage energy. In addition, even if the cleavage of a double strand having no relation with the target material is likely to occur, both the aptamer and the first nucleic acid fragment remain on the member surface. In the absence of the target material, a double bond can be rapidly formed again through the double strand stabilizing step.

On the other hand, as disclosed in Patent Document 1, when either the aptamer or the first nucleic acid fragment is fixed to a substrate, the cleavage of a double strand having no relation with a target material is likely to occur due to the application of a cleavage energy. A nucleic acid fragment or the like which is not fixed is separated from the substrate and is diluted in a solution. Therefore, even after the double strand stabilizing step, a double strand is not formed again, and erroneous detection occurs.

Here, an example of detecting a target material in which the heating of a measurement solution is used in the cleavage energy applying step; and the cooling of a measurement solution is used in the double strand stabilizing step will be described again using FIG. 12.

In FIG. 12(a), a tip of the first nucleic acid fragment 2 is labeled with the labeling material 3. A terminal of the aptamer 1 and a terminal of the first nucleic acid fragment 2 are fixed to the fixing member 4, which is an electrode, thereby forming the complex 11. The fixing member 4 is connected to an electrochemical measuring device along with a counter electrode and a reference electrode which are not illustrated in the drawing.

First, before the complex 11 is brought into contact with a solution of an inspection target, an electrochemical measurement is performed using the fixing member 4 as a working electrode (FIG. 12(a)). In this state, since the aptamer 1 and the first nucleic acid fragment 2 form a double strand, a low current value is observed.

Next, using a heating portion not illustrated in the drawing, the temperature of the measurement solution is increased to a melting temperature of a double strand between the aptamer 1 and the first nucleic acid fragment 2. At this time, half of double strands between the aptamers 1 and the first nucleic acid fragments 2 are dissociated to be in the single-stranded state (FIG. 12(b)). That is, the heating of the measurement solution to the melting temperature refers to the application of a cleavage energy which is equal to a double-strand binding energy.

Next, the inspection target is brought into contact with the complex 11. When the inspection target contains the target material, the target material 7 binds to the aptamer 1 in the single-stranded state (FIG. 12(c)). When the inspection target does not contain the target material 7, the aptamer 1 holds the single-stranded state (FIG. 12(e)).

Next, using a cooling portion not illustrated in the drawing, the temperature of the measurement solution is decreased to room temperature. By cooling the measurement solution, a double-stranded bond between the aptamer 1 and the first nucleic acid fragment 2 is stabilized again. However, when the inspection target contains the target material 7, the aptamer 1 and the target material 7 bind to each other. As a result, the formation of a double strand by the aptamer 1 and the second nucleic acid fragment is inhibited, and the double strand holds the cleaved state (FIG. 12(d)). On the other hand, when the inspection target does not contain the target material 7, the aptamer 1 and the second nucleic acid fragment form a double strand again (FIG. 12(f)).

Next, an electrochemical measurement is performed again using the fixing member 4 as a working electrode. When the inspection target contains the target material 7, a double strand is cleaved, and thus a high reaction current is observed. When the inspection target does not contain the target material 7, a double strand is formed, and thus a low reaction current is observed.

By heating and cooling the measurement solution using the above-described method, the target material can be detected, in which the double strand site is rapidly cleaved in the presence of the target material, and the double strand site is held in the absence of the target material.

The case where the measurement solution is heated to a temperature lower than the melting temperature corresponds to the case where a cleavage energy which is lower than or equal to a binding energy between the aptamer 1 and the first nucleic acid fragment 2 is applied. The effect of weakening a binding strength between the aptamer 1 and the first nucleic acid fragment 2 is obtained as long as the temperature of the measurement solution is higher than a temperature before heating. Therefore, even if the temperature of the measurement solution is lower than the melting temperature, an effect of promoting the rapid cleavage of the double strand site in the presence of the target material is obtained.

In addition, the temperatures after heating is lower than the melting temperature preferably by lower than 10° C. and more preferably by lower than 5° C. The reason is as follows. In this temperature range, a part of the double strand site is cleaved by thermal motions of the aptamer and the nucleic acid fragment. Therefore, this temperature range is suitable for obtaining the effect of promoting the rapid cleavage of the double strand site in the presence of the target material.

EXAMPLES

Hereinafter, the present invention will be described using examples. However, the present invention is not limited to these examples.

Example 1

Detection of ATP

In this example, adenosine triphosphate (hereinafter, referred to as "ATP") was detected with a method of detecting a target material according to the invention using an ATP aptamer to which ATP specifically binds.

An ATP aptamer (sequence 2) and a nucleic acid fragment (sequence 3) complementary to the ATP aptamer which were used in this example are illustrated in FIG. 15. In this example, as the ATP aptamer, a DNA obtained by a method was used, the method including: adding a sequence, incapable of binding to ATP, as a spacer to 5' terminal of a base sequence (sequence 1 of FIG. 15) of the ATP aptamer capable of forming a bond with ATP; and modifying 5' terminal with a thiol group as a functional group for fixing to a substrate. In addition, as the nucleic acid fragment, a DNA was used, the DNA including: 7 bases complementary to sequence 2; and 5 bases non-complementary to sequence 2 as a spacer between the substrate and the nucleic acid fragment, in which 5' terminal was modified by using methylene blue (MB) which was a electrode reactant as a labeling material, and 3' terminal of the DNA was modified by using a thiol group which was a functional group for fixing to the substrate as a labeling material. Sequence 2 and sequence 3 were synthesized using a DNA synthesis service available from Tsukuba Oligo Service Co., Ltd.

The ATP aptamer and the nucleic acid fragment were dissolved in a fixing buffer (20 mM Tris-HCl, 500 mM NaCl, pH 7.4) in each amount of 100 nM. This solution was sealed in a plastic tube, followed by an annealing treatment at 95° C. for 3 minutes. Next, the tube was put in an ice tube for 5 minutes and was left to stand at room temperature for 30 minutes.

A gold electrode (manufactured by BAS Inc.) with a surface cleaned in an alumina polishing treatment was dipped in this solution for 1 hour to fix the ATP aptamer and the nucleic acid fragment to a surface of the gold electrode.

Next, the electrode surface was rinsed with ultrapure water, and was dipped for 1 hour in the fixing buffer in which 1 mM of mercaptohexanol was dissolved, followed by blocking.

After being rinsed with ultrapure water, this electrode was dipped in a glass cell filled with a measurement solution (20 mM tris, 300 mM NaCl, 5 mM $MgCl_2$ (pH 7.4)) and was connected to a working electrode of potentiostat (Compat-Stat, manufactured by Ivium Technologies B.V). In addition, a platinum line was connected to a counter electrode, and a silver-silver chloride electrode (manufactured by BAS Inc.) was connected to a terminal of a reference electrode. Then, using alternating current voltammetry (ACV), the reaction current of methylene blue was measured. The measurement was repetitively performed at intervals of 20 seconds. After 400 seconds from the start of the measurement, ATP was added to the solution such that the final concentration was 1 mM.

Figure 14:
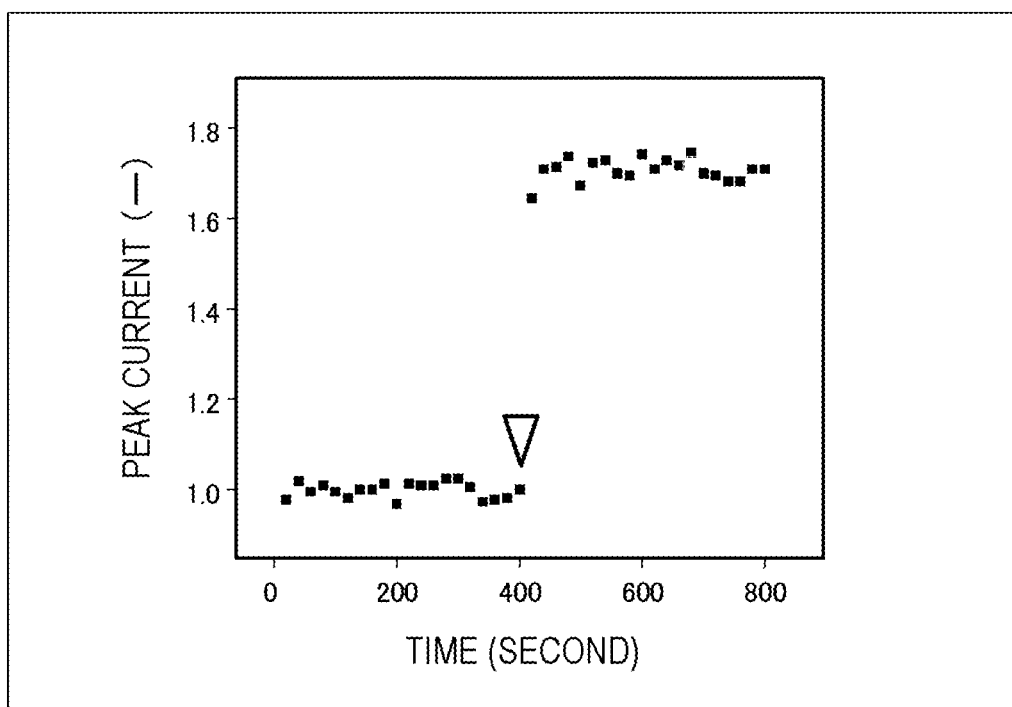
FIG. 14 is a diagram illustrating the measurement results of Example 1.

In the above-described measurement, temporal changes in the peak current of ACV are illustrated in FIG. 14. The current values were normalized based on the peak current immediately before the addition of ATP. The peak current started to increase immediately after the addition of ATP, and was finally approximately 1.7 times that before the addition. Since the current value before the addition of ATP was substantially constant, it can be said that this current increase is specific to ATP.

This result can be described as follows.

The ATP aptamer and the nucleic acid fragment are fixed to the same electrode to be adjacent to each other. As a result, an apparent binding constant is increased, a double-stranded nucleic acid site is formed through a complementary base sequence of 7 bases which wound not form a double-stranded nucleic acid site in the solution. As a result, the mobility of methylene blue labeling the nucleic acid fragment is decreased, the contact frequency between methylene blue and the electrode is decreased, and thus, the reaction current of methylene blue in the ACV measurement is suppressed. Next, when ATP which was a target material of the aptamer is added to the measurement solution, ATP binds to the ATP aptamer, and thus the double-stranded nucleic acid site is cleaved. As a result, the mobility of methylene blue is recovered, and the reaction current of methylene blue in the ACV is increased.

It can be said from the above result that ATP which is the target material can be detected based on the method of detecting a target material according to the present invention by using the electrode which is the member to which the ATP aptamer (sequence 2 of FIG. 15) specifically binding to ATP and the nucleic acid fragment (sequence 3 of FIG. 15) complementary to the ATP aptamer are fixed.

Example 2

Simulation of Embodiment 3

The detection of the cleavage of the double-stranded nucleic acid site between the aptamer and the nucleic acid fragment caused by the addition of the second nucleic acid fragment was investigated by a simulation according to the third exemplary embodiment of the present invention.

When the simulation was performed, sequences 4 to 6 (FIG. 15) were used as DNA sequence conditions. In addition, buffer conditions were (300 mM Na+, 5 mM Mg2+, pH 7.4) and a liquid temperature of 37° C.

In this example, sequence 4 is a DNA in which the ATP aptamer and the nucleic acid fragment complementary to the ATP aptamer are connected, and sequence 5 is the second nucleic acid fragment according to the third exemplary embodiment. In addition, sequence 6 is a base sequence obtained by excluding the base sequence of the aptamer from sequence 4, and corresponds to sequence 4 of which a binding strength to the nucleic acid fragment is lost by the sequence portion of the ATP aptamer binding to ATP. Specifically, in sequence 4, 27 bases specifically binding to ATP; and 7 bases corresponding to the nucleic acid fragment complementary to a part of 27 bases are linked to each other through 13 bases which is a linker of both 27 bases and 13 bases. In addition, sequence 5 includes 7 bases complementary to the entire region of the nucleic acid fragment in sequence 4; and bases complementary to 5 bases which is a linker sequence continuously extending from the nucleic acid fragment.

When DNAs having different base sequences were mixed under the above-described conditions, the easiness of the formation of the double-stranded nucleic acid site by a complementary base sequence was obtained by calculating (refer to Non-Patent Document 5) a secondary structure in which the free energy of DNA was the minimum.

FIG. 16 illustrates the results of obtaining a ratio of an abundance of a DNA where the double-stranded nucleic acid site was formed to an abundance of all the DNAs regarding sequences 4 and 5 and sequences 6 and 5.

When sequences 4 and 5 coexisted, 2% of both sequences formed the double-stranded nucleic acid site through a complementary base sequence. In addition, although not illustrated in FIG. 16, approximately 97% of sequence 4 formed the double-stranded nucleic acid site using the sequence portion of the ATP aptamer and the nucleic acid fragment portion of its own. That is, in this state, the ATP aptamer and the nucleic acid fragment adjacent to each other formed the double strand-forming site. As a result, sequence 5 which was the second nucleic acid fragment did not substantially form the double-stranded nucleic site with the nucleic acid fragment portion of sequence 4.

On the other hand, when sequences 6 and 5 coexisted, 85% of both sequences 6 and 5 formed the double-stranded nucleic acid site. That is, when ATP was added, ATP bound to the base sequence of sequence 4 capable of binding to ATP. As a result, when the double-stranded nucleic acid site between the base sequence and the nucleic acid fragment portion was eliminated, sequence 5 which was the second nucleic acid fragment easily formed the double-stranded nucleic acid site with the nucleic acid fragment of sequence 6.

It can be seen from the above results that the configuration of the third exemplary embodiment in which the second nucleic acid fragment and the nucleic acid fragment do not bind to each other in the absence of the target material and bind to each other in the presence of the target material can be realized.

Example 3

Investigation on Optimum Length of Double-Stranded Nucleic Acid Site

In this example, ATP was detected with the method of detecting a target material according to the present invention by using nucleic acid fragments having different numbers of bases complementary to an ATP aptamer. That is, in this example, when the lengths of the double-stranded nucleic acid sites were different, ATP detecting abilities were compared to each other.

The ATP aptamer (sequence 2) and nucleic acid fragments (sequences 7 and 8) complementary to the ATP aptamer which were used in this example are illustrated in FIG. 15. Sequence 2 is identical to the ATP aptamer of Example 1. The nucleic acid fragment of sequence 7 includes 9 bases complementary to sequence 2; and 5 bases non-complementary to sequence 2 as a spacer. The nucleic acid fragment of sequence 8 includes 5 bases complementary to sequence 2; and 5 bases non-complementary to sequence 2 as a spacer. That is, when sequence 2 and sequence 7 are fixed to the same member, the length of the double-stranded nucleic acid site is 5 bases. In the case of a combination between sequence 2 and sequence 8, the length of the double-stranded nucleic acid site is 9 bases. In the case of a combination between sequence 2 and sequence 3 of Example 1, the length of the double-stranded nucleic acid site is 7 bases.

Sequences 2 and 7; or sequences 2 and 8 were fixed to a gold electrode with the same method as that of Example 1, and ATP was added thereto while performing the ACV measurement such that the final concentration was 1 mM.

Figure 17:
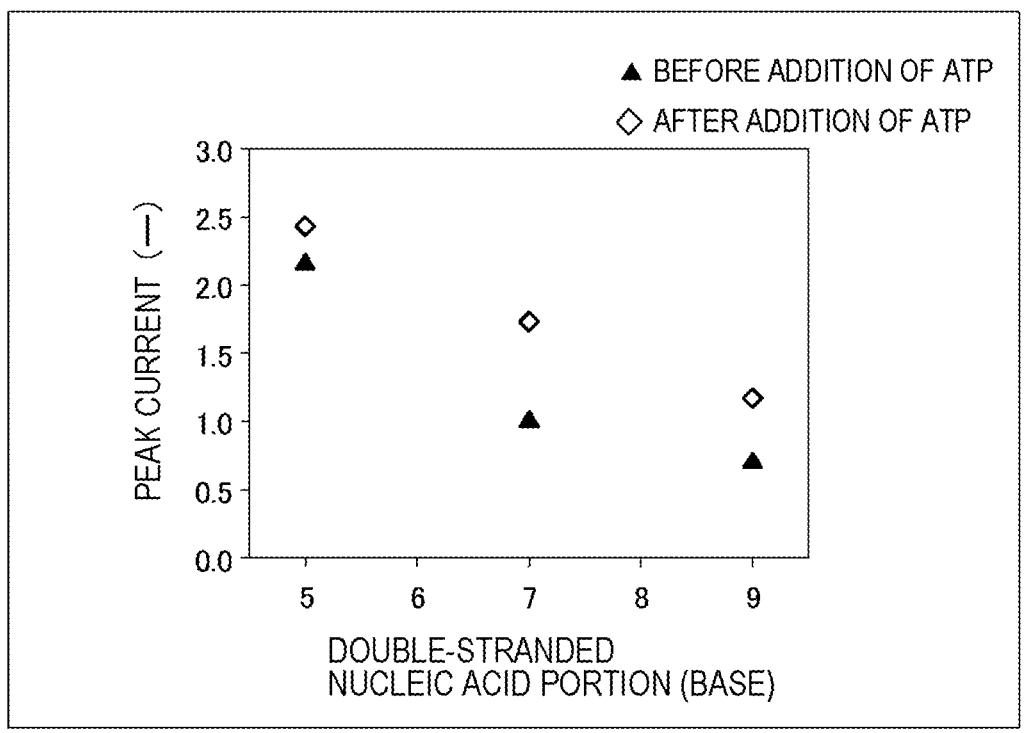
FIG. 17 is a diagram illustrating the measurement results of Example 3.

FIG. 17 illustrates a correlation between the number of bases of the double-stranded nucleic acid site and the peak currents of ACV before the addition of ATP and after 400 seconds from the addition of ATP in the above-described measurement and the measurement of Example 1. The peak currents of ACV were normalized based on the peak current of Example 1 immediately before the addition of ATP.

It was confirmed from FIG. 17 that, in all the cases where the length of the double-stranded nucleic acid site was 5 bases to 9 bases, the current value after the addition of ATP was increased, and the method according to the present invention can be applied to the detection of ATP. However, the amounts of changes in peak current before and after the addition and the changes rates thereof showed the largest values when the length was 7 bases. In addition, when the peak currents of the respective conditions before the addition of ATP are compared to each other, the following tendency was shown: the more the number of bases of the double-stranded nucleic acid site, the lower the current value.

Based on this result, the optimum length of the double-stranded nucleic acid site in the method of detecting a target material according to the present invention can be described as follows.

When the double-stranded nucleic acid site is excessively short, the stability of the double-stranded nucleic acid site is excessively low. Therefore, the forming efficiency of the double-stranded nucleic acid site is significantly decreased. Therefore, the amounts of changes of the double-stranded nucleic acid site before and after the addition of the target material and the change ratios thereof are decreased, which inhibits the high-sensitivity detection of the target material. On the other hand, when the double-stranded nucleic acid site is excessively long, the stability of the double-stranded nucleic acid site is excessively high. Therefore, it is difficult to cleave the double-stranded nucleic acid site even after the addition of the target material. Therefore, the amounts of changes of the double-stranded nucleic acid site before and after the addition of the target material and the changes ratios thereof are decreased, which inhibits the high-sensitivity detection of the target material.

That is, the detection of the target material can be effectively performed by appropriately setting the length of the double-stranded nucleic acid site based on parameters such as the configuration of the base sequence forming the double-stranded nucleic acid site.

Example 4

Investigation on Optimum Length of Spacer

In this example, ATP was detected with the method of detecting a target material according to the present invention by using ATP aptamers and nucleic acid fragments which had different lengths of spacers between the double-stranded nucleic acid site and a substrate. That is, in this example, when the lengths of the spacers were different, ATP detecting abilities were compared to each other.

ATP aptamers (sequences 9 to 11) and nucleic acid fragments (sequences 12 to 14) complementary to the ATP aptamers which were used in this example are illustrated in FIG. 15. Sequences 9 to 11 and sequences 12 to 14 are the same as those of Example 1, except that the lengths of spacer sequences are different. When the ATP aptamer of sequence 9 and the nucleic acid fragment of sequence 12 are fixed to the same member, the length of the spacer is 7 bases. In addition, in the case of a combination between sequence 10 and sequence 13, the length of the spacer is 3 bases. In the case of a combination between sequence 11 and sequence 14, the length of the spacer is 1 base. In all the above-described combinations, the number of bases forming the double-stranded nucleic acid site is 7 bases, and the base sequence thereof is also the same.

Sequences 9 and 12; sequences 10 and 13; or sequences 11 and 14 were fixed to a gold electrode with the same method as that of Example 1, and ATP was added thereto while performing the ACV measurement such that the final concentration was 1 mM.

Figure 18:
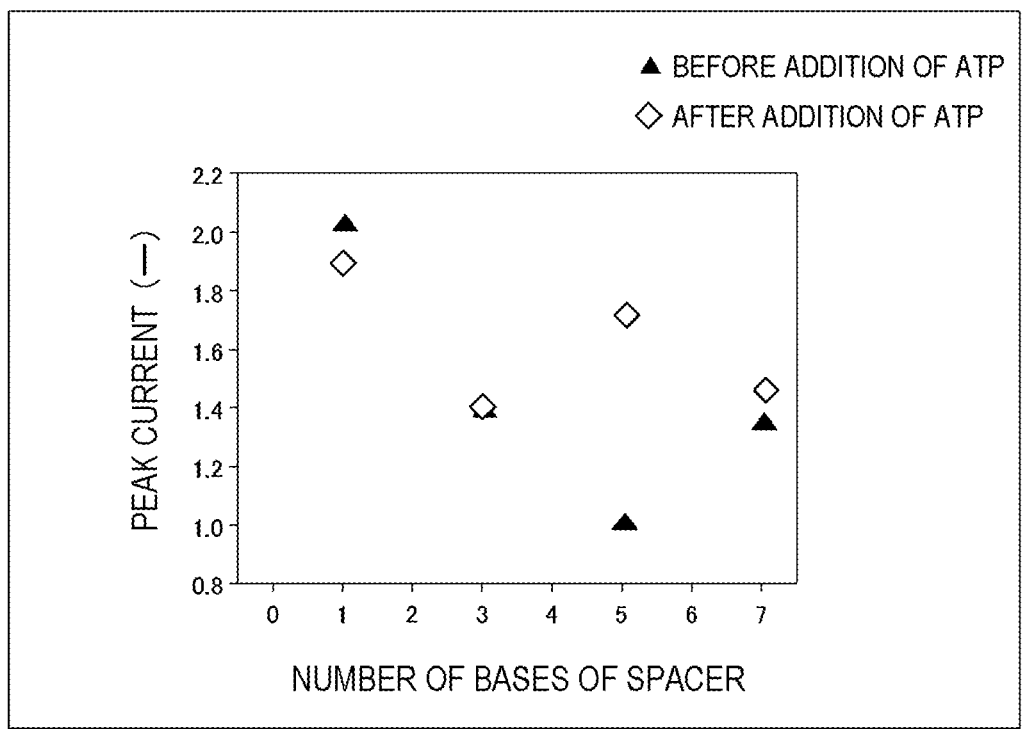
FIG. 18 is a diagram illustrating the measurement results of Example 4.

FIG. 18 illustrates a correlation between the number of bases of the spacer and the peak currents of ACV before the addition of ATP and after 400 seconds from the addition of ATP in the above-described measurement and the measurement of Example 1. The peak currents of ACV were normalized based on the peak current of Example 1 immediately before the addition of ATP.

As illustrated in FIG. 18, when the length of the spacer was 5 bases, a significant increase in current was shown. However, when the length of the spacer was 7 bases, the increase was small, and when the length of the spacer was 1 base or 3 bases, a significant increase in current was not shown after the addition of ATP. In addition, when the length of the spacer was 5 bases, the current value before the addition of ATP was the minimum. In all the cases where the spacer was longer than or shorter than 5 bases, the current value tended to increase.

Based on this result, the optimum length of the spacer in the method of detecting a target material according to the present invention can be described as follows.

When the spacer is excessively short, the bases forming the double-stranded nucleic acid site are positioned to be close to the substrate. As a result, the formation of the double-stranded nucleic site can be inhibited by a strong effect of steric hindrance from the substrate. Therefore, the double-stranded nucleic acid site between the aptamer and the nucleic acid fragment fixed to the substrate is cleaved even before the addition of ATP. In addition, due to the steric hindrance from the substrate, the formation of a secondary structure for forming a bond between the aptamer and the target material is also inhibited. As a result, a bond between ATP and the aptamer cannot be formed even after the addition of ATP, and the cleavage of the double-stranded nucleic acid site does not advance. Due to these effects, when the cleavage of the double-stranded nucleic acid site is detected by an electrochemical reaction of the labeling material modifying the nucleic acid fragment as in the case of this example, a high current which does not depend on the addition of ATP is observed.

On the other hand, when the spacer is excessively long, a concentration effect obtained by fixing the aptamer and the nucleic acid fragment to the member surface to be adjacent to each other is decreased. As a result, the forming efficiency of the double-stranded nucleic acid site is decreased, and the double-stranded nucleic acid site between the aptamer and the nucleic acid fragment fixed to the substrate is cleaved even before the addition of ATP. When the cleavage of the double-stranded nucleic acid site is detected by an electrochemical reaction of the labeling material modifying the nucleic acid fragment as in the case of this example, a high current which does not depend on the addition of ATP is observed.

The structure of the spacer site can be freely changed. Therefore, when the spacer site is long, the labeling material can come into contact with the electrode surface even in a state where the double-stranded nucleic acid site is formed. Accordingly, when the cleavage of the double-stranded nucleic acid site is detected by an electrochemical reaction of the labeling material modifying the nucleic acid fragment as in the case of this example, the effect of the excessively long spacer is significantly large.

That is, by setting the length of the spacer to be an appropriate value, the detection of the target material can be effectively performed.

Example 5

Dependence on Concentration

In this example, using the same aptamer and the nucleic acid fragment as those of Example 1, the ATP concentration and the dependence of the current value on concentration were investigated.

Similarly to Example 1, the ATP aptamer of sequence 2 and the nucleic acid fragment of sequence 3 were fixed to the electrode surface. While performing the ACV measurement using this electrode, ATP was gradually added to the measurement solution.

Figure 19:
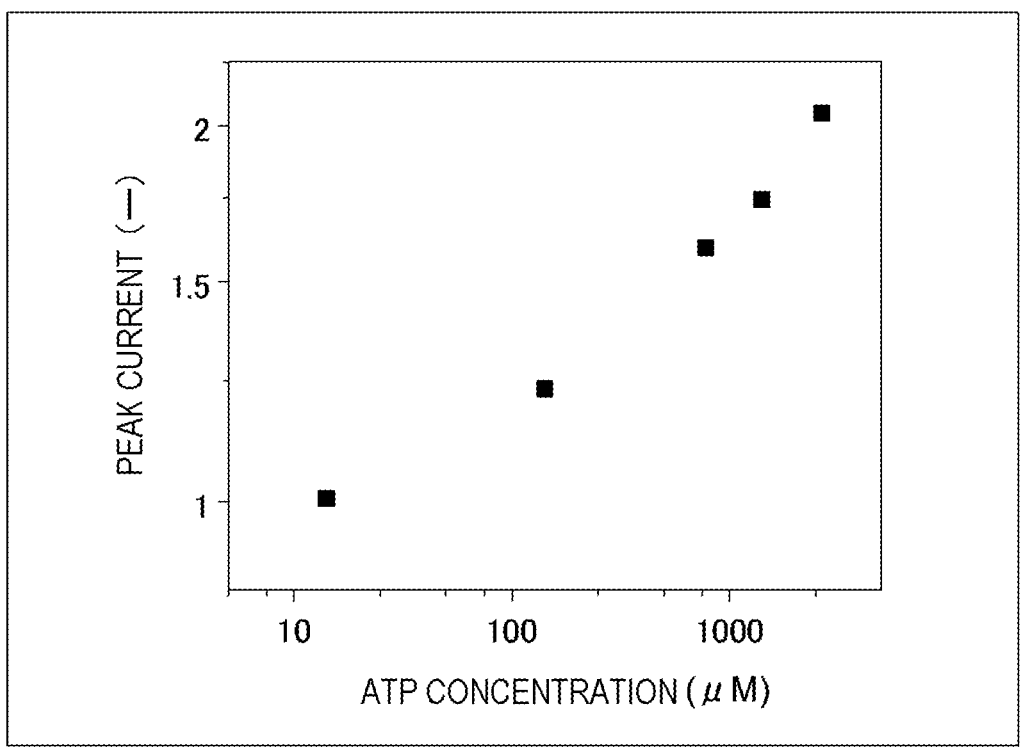
FIG. 19 is a diagram illustrating the measurement results of Example 5.

FIG. 19 illustrates a correlation between the ATP concentration and the peak current. The peak currents were normalized based on the peak current before the addition of ATP.

As illustrated in FIG. 19, the peak current was increased dependent on the ATP concentration. In this way, the target material in the measurement solution can be detected or quantitatively measured by detecting the cleavage of the double-stranded nucleic acid site caused by the labeling material with the method of detecting a target material according to the present invention.

Example 6

In this example, using an ATP aptamer and a nucleic acid fragment which did not contain a spacer sequence, ATP was detected with the method of detecting a target material according to the present invention.

An ATP aptamer (sequence 15); and a nucleic acid fragment (sequence 3) complementary to the ATP aptamer which were used in this example are illustrated in FIG. 15.

Sequence 15 is obtained by changing a spacer sequence portion of the ATP aptamer (sequence 2) used in Example 1 into a base sequence complementary to a portion of sequence 3 used as a spacer. That is, when the ATP aptamer of sequence 15 and the nucleic acid fragment of sequence 3 are fixed to the same member, the length of the spacer is zero, and the number of bases forming the double-stranded nucleic acid site is 12. In addition, 5 bases of the double-stranded nucleic acid site on the substrate side are a margin sequence having no relation with a bond with ATP.

Sequence 15 and sequence 3 were fixed to a gold electrode with the same method as that of Example 1, and ATP was added thereto while performing the ACV measurement such that the final concentration was 1 mM.

Figure 20:
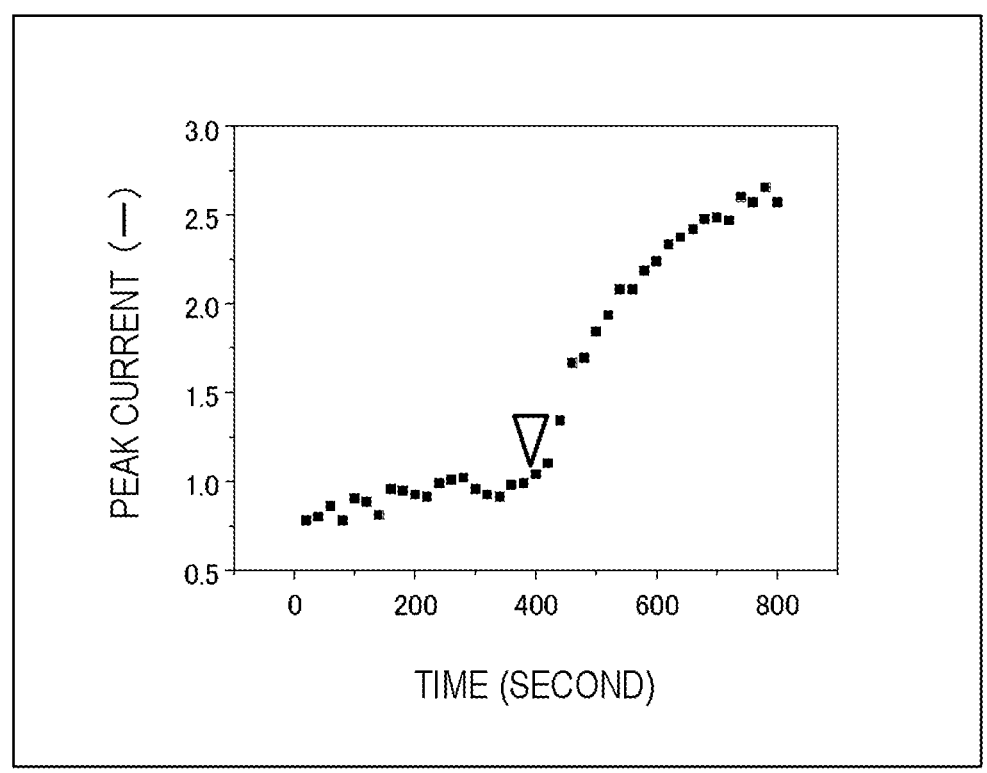
FIG. 20 is a diagram illustrating the measurement results of Example 6.

In the above-described measurement, temporal changes in the peak current of ACV are illustrated in FIG. 20. The current values were normalized based on the peak current immediately before the addition of ATP. The peak current started to increase immediately after the addition of ATP, and was finally approximately 2.5 times that before the addition. Since the current value before the addition of ATP was substantially constant, it can be said that this current increase is specific to ATP.

This result can be described as follows.

That is, the ATP aptamer and the nucleic acid fragment fixed to the electrode forms the double-stranded nucleic acid site through a mutually complementary base sequence. At this time, a base sequence close to the substrate cannot form the double-stranded nucleic acid site due to the steric hindrance with the substrate. However, since a complementary base sequence having a sufficient length for forming a stable double strand site exists at a position distant from the substrate, a low current value is shown before the addition of ATP. Next, when ATP is added, the double-stranded nucleic acid site is cleaved by ATP and the ATP aptamer binding to each other, and the current value is increased.

As described above, the optimum length of the spacer in the method of detecting a target material according to the present invention changes depending on the number of complementary base capable of forming the double-stranded nucleic acid site, and the spacer sequence may not be provided.

In addition, in the method of detecting a target material according to the present invention, the double-stranded nucleic acid site may contain a margin sequence having no relation with a bond with the target material.

It is needless to say that the above-described embodiments and plural modification examples can be combined within a range where the contents thereof are not contradictory to each other. In addition, in the above-described embodiments and modification examples, the structure of each portion and the like have been specifically described, but the structure and the like can be modified in various ways within a range satisfying the scope of the present invention.

Priority is claimed on Japanese Patent Application No. 2011-162023, filed Jul. 25, 2011 and Japanese Patent Application No. 2012-046589, filed Mar. 2, 2012, the contents of which are incorporated herein by reference.

The invention claimed is:

1. A method of detecting a target material, the method comprising:
   a step of preparing a complex, the complex including
   an aptamer to which a target material in a specimen specifically binds,
   a first nucleic acid fragment that has a base sequence complementary to the aptamer, and
   a fixing member to which a part of the aptamer and a part of the first nucleic acid fragment are fixed,
   in which the aptamer has a double strand-forming site capable of forming a double strand with the first nucleic acid fragment;
   a step of separating the first nucleic acid fragment from the double strand-forming site of the aptamer by binding the target material to the aptamer; and
   a step of detecting cleavage of the double strand where the first nucleic acid fragment is separated from the aptamer;
   wherein a base sequence of the aptamer to which the target material binds comprises at least a part of a base sequence of a double strand-forming site formed between the aptamer and the first nucleic acid fragment.

2. The method of detecting a target material according to claim 1,
   wherein the double strand-forming site of the aptamer has only a base sequence complementary to the base sequence of the first nucleic acid fragment.

3. The method of detecting a target material according to claim 1,
   wherein the complex includes a linking portion through which a part of the aptamer and a part of the first nucleic acid fragment are linked to each other, and
   the linking portion is fixed to the fixing member.

4. The method of detecting a target material according to claim 1,
   wherein the step of detecting the cleavage of the double strand includes
   a step of binding a second nucleic acid fragment, which has a base sequence complementary to the first nucleic acid fragment, to the first nucleic acid fragment which is separated from the double strand-forming site, and
   a step of detecting a bond between the first nucleic acid fragment and the second nucleic acid fragment to detect the cleavage of the double strand.

5. The method of detecting a target material according to claim 4,
   wherein the fixing member has a solvophilic region in a different region from a fixing region where the aptamer and the first nucleic acid fragment are fixed.

6. The method of detecting a target material according to claim 4,
   wherein the step of binding a second nucleic acid fragment includes a step of binding the second nucleic acid fragment, which is fixed to a substrate, to the first nucleic acid fragment which is separated from the double strand-forming site, and
   the substrate has a solvophilic region in a different region from a fixing region where the second nucleic acid fragment is fixed.

7. The method of detecting a target material according to claim 1, further comprising:
   a cleavage energy applying step of applying a cleavage energy, which is higher than or equal to a binding energy of a double strand between the aptamer and the first nucleic acid fragment, before or during the step of separating the first nucleic acid fragment from the double strand-forming site of the aptamer; and
   a double strand stabilizing step of strengthening a binding strength of a double strand between the aptamer and the first nucleic acid fragment, before or during the step of detecting the cleavage of the double strand;
   wherein the cleavage energy applying step comprises heating a measurement solution.

8. The method of detecting a target material according to claim 1, further comprising:
   a cleavage energy applying step of applying a cleavage energy, which is lower than a binding energy of a double strand between the aptamer and the first nucleic acid fragment, before or during the step of separating the first nucleic acid fragment from the double strand-forming site of the aptamer; and
   a double strand stabilizing step of strengthening a binding strength of a double strand between the aptamer and the first nucleic acid fragment, before or during the step of detecting the cleavage of the double strand;
   wherein the double strand stabilizing step comprises cooling a measurement solution.

* * * * *

SEQUENCE LISTING

```
<160> NUMBER OF SEQ ID NOS: 15

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      ATP aptamer

<400> SEQUENCE: 1
acctggggga gtattgcgga ggaaggt                                           27

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      ATP aptamer with spacer

<400> SEQUENCE: 2
cactgacctg ggggagtatt gcggaggaag gt                                     32

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 3
cccaggttct ct                                                           12

<210> SEQ ID NO 4
```

```
<211> LENGTH: 47
<212> TYPE: DNA
<213> ORGANISM: Artificial Sequence
<220> FEATURE:
<223> OTHER INFORMATION: Description of Artificial Sequence: Synthetic
      ATP aptamer linked with its complementary strand

<400> SEQUENCE: 4
cccaggttct ctttttttt acctggggga gtattgcgga ggaaggt              47

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agagaacctg gg                                                   12

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide minus the sequence of ATP aptamer

<400> SEQUENCE: 6
cccaggttct ctttttttt                                            20

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 7
cccccaggtt ctct                                                 14

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 8
caggttctct                                                      10

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      ATP aptamer with spacer

<400> SEQUENCE: 9
ttcactgacc tgggggagta ttgcggagga aggt                           34

<210> SEQ ID NO 10
<211> LENGTH: 30
```

-continued

<212> TYPE: DNA
<213> ORGANISM: Artificial Sequence
<220> FEATURE:
<223> OTHER INFORMATION: Description of Artificial Sequence: Synthetic
      ATP aptamer with spacer

<400> SEQUENCE: 10
ctgacctggg ggagtattgc ggaggaaggt                                      30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      ATP aptamer with spacer

<400> SEQUENCE: 11
gacctggggg agtattgcgg aggaaggt                                        28

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 12
cccaggttct cttt                                                       14

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 13
cccaggttct                                                            10

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide partly complementary to ATP aptamer

<400> SEQUENCE: 14 cccaggtt                                                               8

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      ATP aptamer with overhang sequence for stronger hybridization

<400> SEQUENCE: 15
agagaacctg ggggagtatt gcggaggaag gt                                   32